United States Patent
Barron et al.

(10) Patent No.: US 6,322,890 B1
(45) Date of Patent: Nov. 27, 2001

(54) SUPRA-MOLECULAR ALKYLALUMOXANES

(75) Inventors: Andrew Ross Barron; Stephen J. Obrey, both of Houston, TX (US)

(73) Assignee: Wm. Marsh Rice University, Houston, TX (US)

( * ) Notice: Subject to any disclaimer, the term of this patent is extended or adjusted under 35 U.S.C. 154(b) by 0 days.

(21) Appl. No.: 09/277,642

(22) Filed: Mar. 26, 1999

Related U.S. Application Data

(60) Provisional application No. 60/079,907, filed on Mar. 30, 1998.

(51) Int. Cl.[7] .................................. B32B 5/16; C07F 5/06

(52) U.S. Cl. .......................... 428/402; 428/403; 556/179

(58) Field of Search .................................. 428/402, 403; 556/179

(56) References Cited

U.S. PATENT DOCUMENTS

| | | | |
|---|---|---|---|
| 3,242,099 | 3/1966 | Manyik | 252/429 |
| 4,133,944 | 1/1979 | Cooper et al. | 526/65 |
| 4,952,714 | * 8/1990 | Welborn | 556/179 |
| 5,032,562 | 7/1991 | Lo et al. | 502/111 |
| 5,157,137 | * 10/1992 | Sangokoya | 556/179 |
| 5,332,706 | 7/1994 | Nowlin et al. | 502/107 |
| 5,391,529 | 2/1995 | Sangokoya | 502/103 |
| 5,473,028 | 12/1995 | Nowlin et al. | 526/114 |
| 5,527,930 | * 6/1996 | Sangokoya | 558/179 |
| 5,565,395 | * 10/1996 | Sangokoya | 502/103 |
| 5,602,067 | 2/1997 | Nowlin et al. | 502/104 |
| 5,693,838 | * 12/1997 | Sangokoya et al. | 556/179 |
| 5,731,451 | 3/1998 | Smith et al. | 556/173 |
| 5,902,766 | * 5/1999 | Butler et al. | 502/152 |
| 6,034,024 | * 3/2000 | Krzystowczyk et al. | 502/107 |

OTHER PUBLICATIONS

Anderson, A., Cordes, H.–G., Herwig, J., Kaminsky, W., Merck, A., Mottweiler, R., Pein, J., Sinn, H., and Vollmer, H.–J., *Angew. Chem. Int. Ed. Engl.,* 15, 630 (1976).

Apblett, Allen W., Warren, Alison C., and Barron, Andrew R., *Reprinted from Chemistry of Materials,* 1992, 4.

Boleslawski, M., Pasynkiewicz, S., Jaworski, K., and Sadownik, A., *J. Organomet. Chem.,* 97, 15 (1975).

Boor, John Jr. *Ziegler–Natta Catalysts and Polymerizations* (1979).

Callender, R. L. Harlan, C.J. Shapiro, N.M. Jones, C.D. Callahan, D.L., Weisner, M.R. Cook, R. Barron, A.R. *Chem. Mater.,* 1997, 9, 2418.

Chaplin, R. P., Burford, R. P., Tory, G. J., and Kirby, S., *1418 Polymer,* 1987, vol. 28, Jul.

Colclough, R. O., *J. Polym. Sci.* 1959, 34, 178.

Dahmen, Klaus–Hermann, Hedden, David, Robert L. Burwell, Jr., and Marks, Tobin J., *Langmuir* 1988, 4, 1212–1214.

Eisch, J.J., *Comprehensive Organometallic Chemistry,* Pergamon Press, Oxford, United Kingdom, 1982, vol. 4 Chap. 6, 555–682.

(List continued on next page.)

*Primary Examiner*—Hoa T. Le

(57) ABSTRACT

Heterogeneous solid supra-molecular alkylalumoxanes. A supra-molecular architecture of a nano-particle foundation on which an alkylalumoxane is built. Supra-molecular alkylalumoxanes comprise (a) an aluminum-oxide nanoparticle, (b) a linkage unit, and (c) an alkylalumoxane. Supra-molecular alkylalumoxanes are prepared by the reaction of a chemically modified aluminum-oxygen nanoparticle with either a pre-formed alkylalumoxane or an alkylaluminum compound, with subsequent hydrolysis or reaction with other alkylalumoxane yielding reagents. The supra-molecular alkylalumoxanes are active as catalysts for the polymerization of organic monomers and as co-catalysts with transition metal components for the polymerization of olefins.

25 Claims, 23 Drawing Sheets-

OTHER PUBLICATIONS

Folkers, John P., Gorman, Christopher B., Laibinis, Paul E., Buchholz, Stefan, and Whitesides, George M., *Langmuir,* 1995, 11, 813–824.

Gurian, P., Cheatham, L.K., Ziller J.W., and Barron, A.R., *J. Chem. Soc., Dalton Trans.,* 1449 (1991).

Harlan, C.J., Mason,M.R., and Barron, A.R., *Organometallics,* 13, 2957 (1994).

Harlan, Jeff C., Bott, Simon G., and Barron, Andrew R., *J. Am. Chem. Soc.,* 117, 6465–6474 (1995).

Harney, D.W., Meisters, A., and Mole, T., *Aust. J. Chem.,* 27, 1639 (1974).

Kaminsky, W., Miri, M., Sinn, H., and Woldt, R., *Makromol. Chem. Rapid Commun.,* 4, 417 (1983).

Kaminsky, Walter, *J. Chem. Soc., Dalton Trans.,* 1998, 1413–1418.

Karol, Frederick J., Karapinka, George L., Wu, Chisung, Dow, Alan W., Johnson, Robert N., and Carrick, Wayne L., *Journal of Polymer Science,* Part A–1, vol. 10, 2621–2637 (1972).

Kushi, Y. and Fernando, O., *J. Chem. Soc., Chem. Sommun.,* 555 (1969).

Landry, C.C.; Davis. J.A.; Apblett, A.W.; Barron, A.R., *J. Mater. Chem.,* 3, 597 (1993).

Larock, R.C., *Comprehensive Organic Transformation,* VCH, New York (1989).

Long, W.P. and Breslow, D.S., *Leibigs Ann. Chem.,* 463 (1975).

Longiave C; Castelli, R., *J. Polym. Sci.,* 1963, 4C, 387.

Mason, M.R. Smith, J.M. Bott, S.G., and Barron A.R., *J. Am. Chem. Soc.,* 115, 4971 (1993).

Pajerski, A. D. and Lenz, R. J., *Makromol. Chem. Macromol. Symp.,* 1993, 73, 7.

Razuvaev, G. A., Sangalov, Yu. A., Nel'kenbaum, Yu, Ya, and Minsker, K. S., *Izv. Akad. Nauk SSSR, Ser. Chim.,* 2547 (1975).

Reichert, K. H. and Meyer, K. R., *Macromol. Chem.,* 169, 163 (1973).

Roscoe, Stephen B., Frechet, Jean M., Walzer, John F., and Dias, Anthony J., *Science,* vol. 280, (1998).

Saegusa, T., Fujii, Y., H.; Furukawa, J., *Makromolek. Chem.,* 1962, 55, 232.

Sakharovskaya, G.B., Korneev, N. N., Popov, A. F., Kissin, Yu. V., Mezhkovskii, S. M., and Kristalanyi, E., *Zh. Obshch. Khim.,* 39, 788 (1969).

Schwartz, Jeffrey and Ward, Michael D., *Journal of Molecular Catalysis,* 8 (1980) 465–469.

Sinn, H. and Kaminsky, W., *Adv. Organomet. Chem,* 18, 99 (1980).

Slotfeldt–Ellingsen, Dag, Dahl, Ivar M., and Ellestad, Ole. H., *Journal of Molecular Catalysis,* 9 (1980) 423–434.

Ueyama, N., Araki, T., and Tani, H., *Inorg. Chem.,* 12, 2218 (1973).

Vandenberg, E.J., *J. Polym. Sci.* 1960, 47, 489.

Vogtle, F., *Supramolecular Chemistry,* Wiley, New York (1991).

Wilkinson, G.; Stone, F. G. A.; Abel, E. W.; *Comprehensive Organometallic Chemistry,* Pergamon Press (1983).

Winter, H., Schnuchel, W., and Sinn, H., *Macromol. Symp.* 97, 119 (1995).

Wynne, K. Y., *Inorg. Chem.,* 24, 1339 (1985).

Ziegler, K., *Angew. Chem.,* 68, 721 (1956).

* cited by examiner

Fig. 7   Solid State NMR of methylalumoxane-hydroxybenzenate-alumoxane

Fig. 9  Thermogravimetric Analysis of a Polyethylene Derived from the Reaction of Ethylene with Methylalumoxane-hydroxybenzoate alumoxane / $Cp_2ZrCl_2$ Fig. 10 Expanded View of Thermogravimetric Analysis of Figure 9

Solid State NMR of polyethylene derived from reaction of methylalumoxane-hydroxybenzenate-alumoxane

Supra-Molecular Alkyl-Alumoxanes

Fig. 13

- Alkyl alumoxanes are highly active co-catalysts for olefin polymerization in combination with group 4, 5, and 6 elements.

- Homogeneous polyolefin catalysts involve alumoxane to transition metal concentrations of 1000:1.

- Silica based heterogeneous olefin polymerization catalysts have lowered the alumoxane to trasition metal relative ratio.

- These silica based heterogeneous catalysts contain particles in the range of 10-100μm, which limits the number of possible catalyst sites per unit volume.

- Development of heterogeneous polymerization catalyst supports on the nanometer scale allow maximum activity per unit volume.

Fig. 14

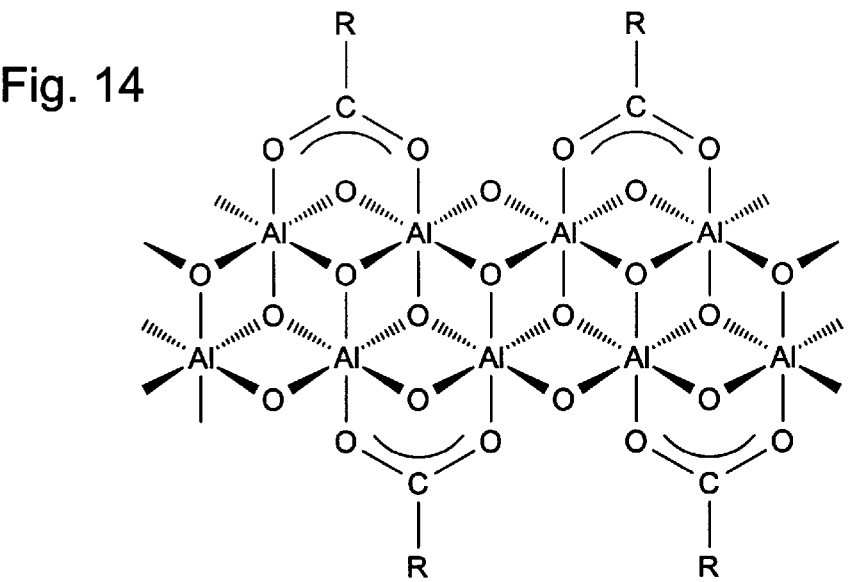

What are Carboxylate-Alumoxanes?

Carboxylate-Alumoxanes are nano-scale aluminum oxide particles with surface carboxylate groups bridging two aluminum atoms. They may be synthesized inexpensively by the reaction of boehmite with carboxylic acids which provides a variety of different surface characteristics. Particles of carboxylate-alumoxanes range in size from 50 to 100nm.

Fig. 15
Structure and Reactivity of Alkyl-Alumoxanes
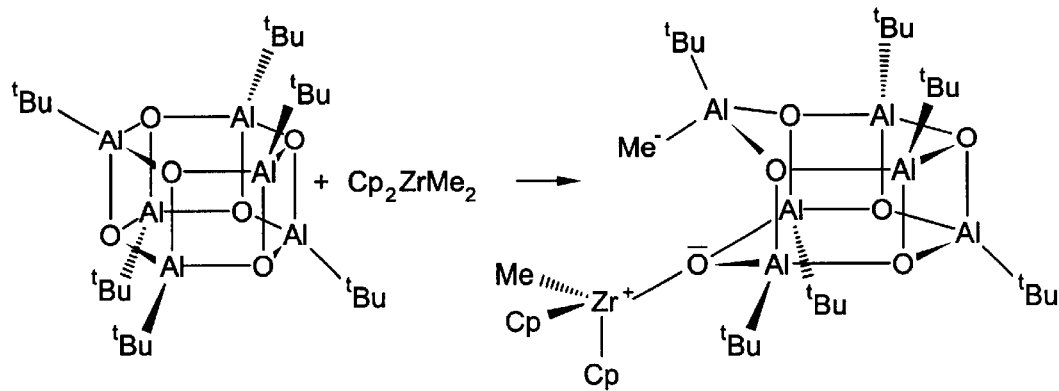
Structure and Reactivity of methyl alumoxane is analogous to [$^t$BuAlO]$_n$ compunds
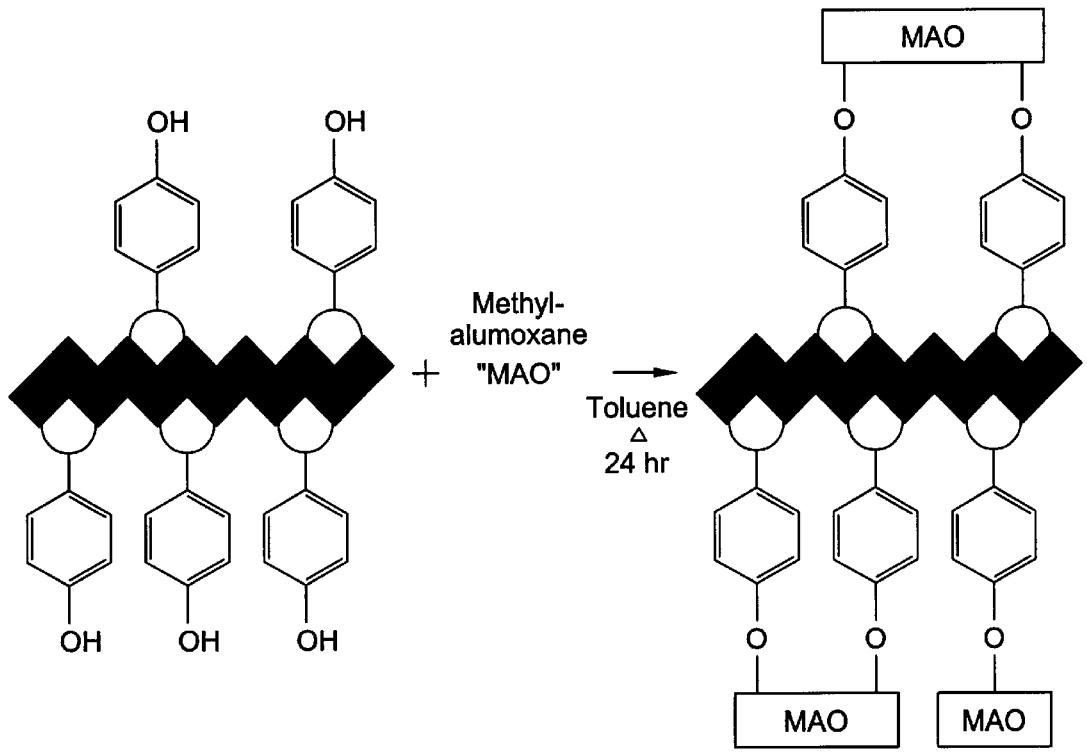
Fig. 17  Synthesis of Supra-Molecular Alkyl-Alumoxanes Synthesis of 4-hydroxybenzoate alumoxane

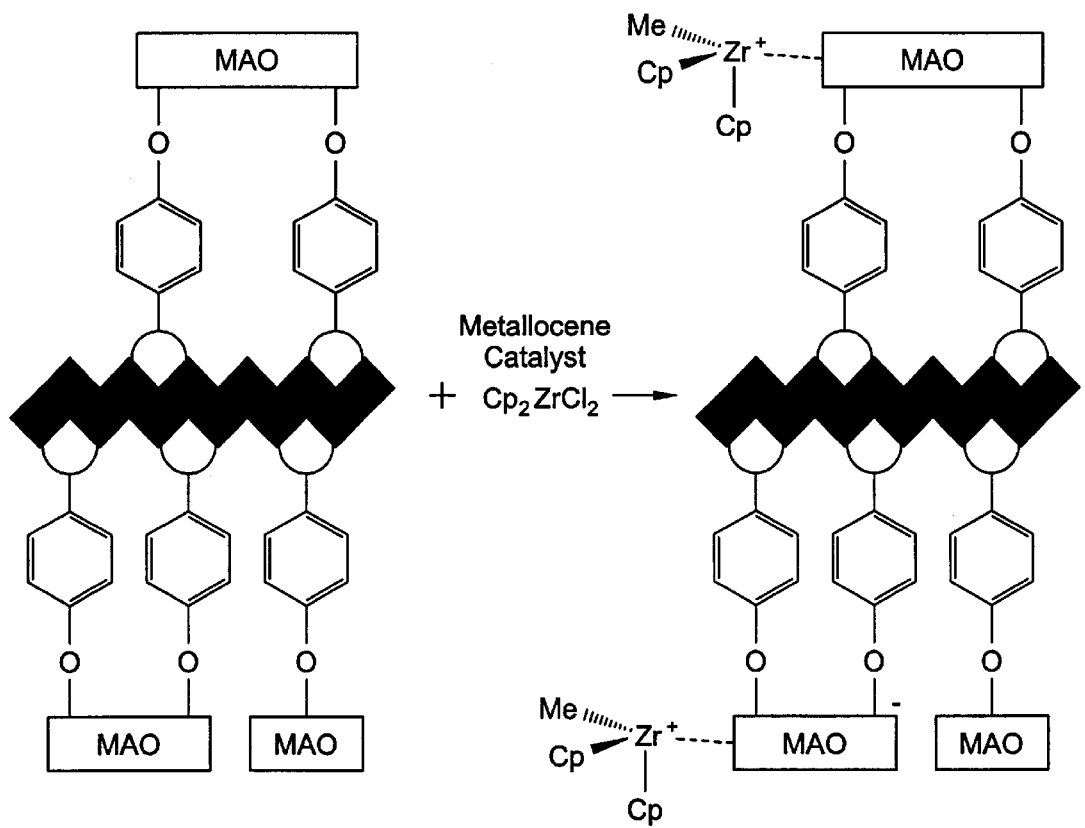
Fig. 18   Synthesis of Polymerization Active Catalyst
Fig. 21   Solid State NMR of Supported Solid Catalyst
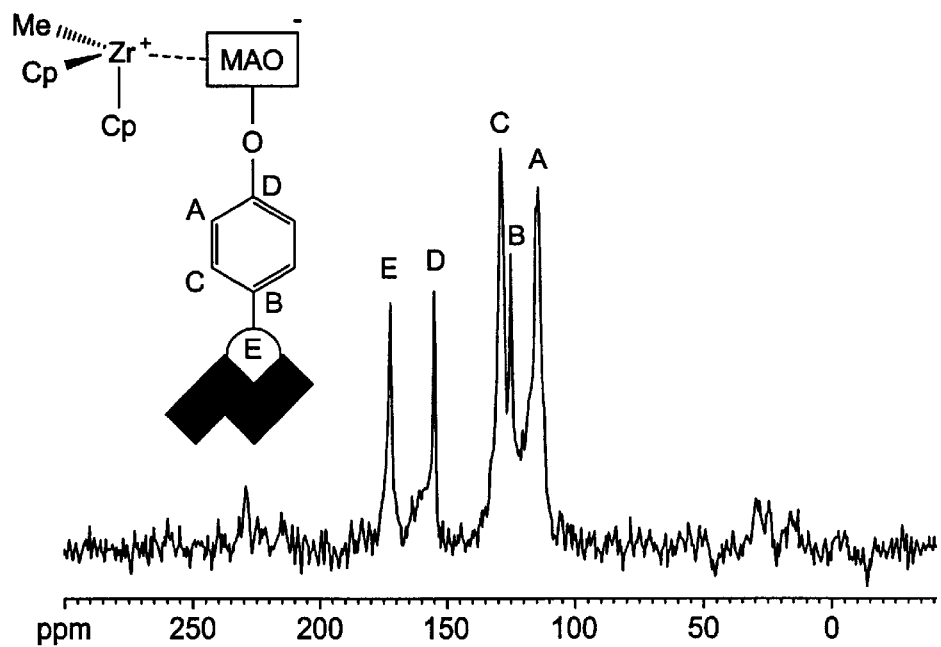

Polymerization of Ethylene

| Solvent (20 ml) | Co-Catalyst (100mg) | Catalyst (1 mg) | mp (°C) | Δmp (°C) | Activity (kg/mol*hr) | Residue |
|---|---|---|---|---|---|---|
| Toluene | Alumoxane | ------------- | ------ | ------ | ------------ | 22.8% |
| Toluene | Alkyl-Alumoxane | ------------- | ------ | ------ | ------------ | 74.8% |
| Toluene | Alkyl-Alumoxane | $Cp_2ZrCl_2$ | 132 | 17.5 | 1601 | 3.9% |
| Toluene | Alkyl-Alumoxane | $(n\text{-}BuCp)_2ZrCl_2$ | 134 | 15.8 | 1730 | 2.6% |
| Toluene | MAO | $Cp_2ZrCl_2$ | 133 | 16.2 | 962 | 14.3% |

| Polyethylene | | Extruded Polyethylene |
|---|---|---|

Solid State NMR of Polyethylene from Supported Solid Catalyst

SUPRA-MOLECULAR ALKYLALUMOXANES

CROSS-REFERENCED TO RELATED APPLICATIONS

This application claims the benefit of U.S. provisional patent application Ser. No. 60/079,907, filed Mar. 30, 1998, which is incorporated herein by reference in its entirety.

STATEMENT REGARDING FEDERALLY SPONSORED RESEARCH OR DEVELOPMENT

Not applicable.

BACKGROUND OF THE INVENTION

1. Field of the Invention

This invention relates generally to a new form of solid supra-molecular alkylalumoxane that can be used as a catalyst or catalyst component. A new form of alkylalumoxane may be prepared using the carboxylate-substituted aluminum-oxygen nano-particles as a template. The invention particularly relates to a new heterogeneous solid catalyst which may be used as a catalyst component for the polymerization of organic monomers or in combination with a transition metal for the polymerization of olefins.

2. Description of the Related Art

The term "alumoxane" is used to describe a molecular species containing at least one oxo group ($O^{2-}$) bridging (at least) two aluminum atoms, i.e., a compound containing an Al—O—Al sub-unit. The simplest alumoxane compounds are those containing two aluminum atoms bridged by a single oxygen with n additional ligands (X) bonded to aluminum (FIG. 1), Gurian et al. (1991), Wynne (1985), Kushi and Frenando (1969). Within the overall definition, the term "alumoxane" is commonly used, (especially with regard to metallocene catalysis), to denote compounds in which the pendant groups on aluminum are organic radical substituents, i.e., alkylalumoxanes. Although alkylalumoxanes are also simply referred to as alumoxanes, this class of compounds actually includes such materials as sol-gels and antiperspirants with no co-catalytic activity. Alumoxanes are also known with a variety of organic and inorganic substituents. For example, carboxylates ($RCO_2$), alkoxides ($RO$) and chlorides (Landry et al. 1993).

Alkylalumoxanes are, therefore, oligomeric aluminum compounds which can be represented by the general formulae $[(R)Al(O)]_n$ and $R[(R)Al(O)]_n AlR_2$. In these formulae, R is an alkyl group, such as methyl ($CH_3$), ethyl ($C_2H_5$), propyl ($C_3H_7$), butyl ($C_4H_9$) or pentyl ($C_5H_{11}$) and n is an integer. Such compounds can be derived from the hydrolysis of alkylaluminum compounds, $AlR_3$. Recent reports indicate that alkylalumoxanes of the formula $[(R)Al(O)]_n$ are generally cage compounds (FIG. 2), Mason et al. (1993) Harlan et al. (1994). It should be noted that while "alkylalumoxane" is generally accepted, alternative terms are found in the literature, such as: alkylaluminoxane, poly(alkylalumoxane), poly(alkylaluminum oxide), and poly(hydrocarbylaluminum oxide). As used herein, the term alkylalumoxane is intended to include all of the foregoing.

Alkylalumoxanes have been prepared in a variety of ways. They can be synthesized by contacting water with a solution of trialkylaluminum, $AlR_3$, in a suitable organic solvent such as an aromatic or an aliphatic hydrocarbon. Alternatively, a trialkylaluminum can be reacted with a hydrated salt such as hydrated aluminum sulfate. In both cases, the reaction is evidenced by the evolution of the appropriate hydrocarbon, i.e., methane ($CH_4$) during the hydrolysis of trimethylaluminum ($AlMe_3$). While these two routes are by far the most common, several "non hydrolysis" routes have been developed.

Conceptually, the simplest route to alkylalumoxanes involves the reaction of water with a trialkylaluminum compound. Simply reacting water or ice (Winter et al. 1995) with an aromatic or aliphatic hydrocarbon solution of a trialkylaluminum will yield an alkylalumoxane. However, it is important to control the temperature of this highly exothermic reaction, both as a safety precaution and in order to maximize the yield and ensure the solubility of the products (Sakharovskaya et al. 1969). Several researchers have employed hydrated salts, such as $Al_2(SO_4)_3.14(H_2O)$ or $CuSO_4.5(H_2O)$, as "indirect hydrolysis" sources (Razuvaev et al. 1975), since the water of crystallization in a hydrated salt reacts at a vastly decreased rate as compared to dissolved "free" water.

There is also a wide range of non-hydrolysis reactions that allow for the formation of alkylalumoxanes. Ziegler in 1956 first reported the formation of an alumoxane from the reaction of triethylaluminum with $CO_2$. Similar product is formed from the reaction of aluminum alkyls with carboxylates and amides (Harney et al. 1974). Alkylalumoxanes may also be prepared by the reaction of main group oxides (Boleslawski et al. 1975), while alkali metal aluminates formed from the reaction of trialkylaluminum with alkali metal hydroxides react with aluminum chlorides to yield alkylalumoxanes (Ueyama et al. 1973)

Alkylalumoxanes are active catalysts in the polymerization of epoxides (Colclough, 1959, Vandenberg, 1960), aldehydes (Saegusa, 1962), olefins (Longiave, 1963), and lactones (Pajerski and Lenz, 1993). Although it has been known since the 1950's that compounds of aluminum react with water to give compounds containing aluminum-oxygen bonds, commonly termed alumoxanes, it was not until the work of Manyik et al. (1966) that their application to olefin catalysis was fully appreciated. These workers showed that alkyl-substituted alumoxanes (alkylalumoxanes) were highly active co-catalysts for olefin polymerization in combination with compounds of the Group 4, 5, and 6 transition metal elements, including metallocenes containing the cyclopentadienyl ligand or substituted cyclopentadienyl ligands. Subsequent work by Reichert and Meyer (1973), Long and Breslow (1975) and Andreson et al. (1976) showed that the addition of water to the soluble metallocene/alkylaluminum catalyst systems resulted in a large increase in catalyst activity. The in-situ formation of alumoxanes in all of these systems was recognized, however, by the high catalytic activity of a metallocene and preformed methylalumoxane system as shown by the work of Andreson et al. (1976) and Kaminsky and Sinn (1980). Kaminsky et al. (1983) also demonstrated that zirconium metallocenes were more active than the titanium metallocenes.

Alkylalumoxane catalysts and co-catalyst systems suffer from a number of disadvantages. Alkylalumoxanes (especially those with methyl, ethyl and butyl substituents) are generally air sensitive, since they contains significant amounts of trialkylaluminum. For example, methylalumoxane ordinarily contains 5–15% of trimethylaluminum. A disadvantage in the homogeneous catalysts and catalyst systems involving transition metals is that the ratio of alkylalumoxane to transition metal compound, for example a metallocene, is about 1,000 to 1 or greater. Such large amounts of alkylalumoxane have several drawbacks. First, alkylalumoxanes such as methylalumoxane are costly to produce, making the economics of catalyst synthesis with respect to the end-product important. Second, the polymer made using such catalyst systems must be treated to remove the aluminum or inhibit its detrimental effects with stabilizers, dyes, and additives. A further disadvantage of homogeneous alkylalumoxane catalyst systems is that multiple delivery systems must be employed to introduce each of the components of the catalyst system into the reaction vessel because of the instability of liquid mixtures of the catalyst components.

Efforts to overcome these issues have included supporting or reacting methylalumoxane with traditional catalyst supports (Welborn, 1989). A typical support used is silica, either dehydrated or hydrated, or some other oxide. The alkylalumoxane is physically adsorbed on the surface of the support and then reacted with the metallocene. The alkylalumoxane may also be pre-reacted with the metallocene, and the product of this reaction further reacted with the surface of the silica. In each case, the alkylalumoxane:metal ratio is decreased with respect to the analogous homogenous catalyst system. However, in each case the supported or solid catalyst comprises particles in the range of 10–100 $\mu$m, which limits the number of possible catalytic sites per unit mass (or volume) of the catalyst. It is highly desirable to produce solid or supported catalysts with an increased activity per unit mass or volume. In order for this to be possible, the solid catalyst must be as small as possible.

SUMMARY OF THE INVENTION

The present invention provides an improved supported catalyst system and features a method for preparation of a solid alkylalumoxane catalyst/co-catalyst component with a particle size in the nanometer range. The method includes the construction of a solid alkylalumoxane with the construction of a supra-molecular architecture. Supra-molecular structures are ordinarily defined as those in which intermolecular bonding occurs between two or more molecules and where the supra-molecular structure has a specific characteristic function or property (Vögtle, 1991). Carboxylate-alumoxanes are synthesized with functionalized substituents that allow for the subsequent construction of alkylalumoxanes. The overall structure of the solid supra-molecular alkylalumoxanes is shown in FIG. 3.

The solid supra-molecular alkylalumoxanes may be used as catalysts for the polymerization of organic monomers such as epoxides and lactones. Further, in combination with a transition metal, the solid supra-molecular alkylalumoxanes are active components in catalyst systems for the polymerization of olefins, including ethylene, and the co-polymerization of ethylene and carbon monoxide. The solid supra-molecular alkylalumoxanes may be used as substitutes for both homogeneous alkylalumoxanes or supported alkylalumoxanes.

Accordingly, the present invention includes in a preferred embodiment a supra-molecular alkylalumoxane comprising a nanoparticle and an alumoxane. In another preferred embodiment the invention includes a catalyst system comprising the reaction product of a substituted or unsubstituted group IV metallocene and a supra-molecular alumoxane, the supra-molecular alumoxane comprising a nanoparticle and an alumoxane. In yet another preferred embodiment the invention includes a method for preparing a supra-molecular alumoxane, comprising the steps of reacting an aluminum-oxide nanoparticle with a carboxylic acid to make a chemically modified aluminum-oxide nanoparticle and reacting the chemically modified aluminum-oxide nanoparticle with an alumoxane. In yet another preferred embodiment the invention includes a catalyst system for the polymerization of olefins comprising the reaction product of a substituted or unsubstituted Group IV metallocene with a supra-molecular alkylalumoxane, and a process for the polymerization of olefins in the presence of such a catalyst system.

BRIEF DESCRIPTION OF THE DRAWINGS

For a more detailed description of the preferred embodiments of the present invention, reference will now be made to the accompanying drawings, wherein:

FIG. 13 Supra-Molecular Alkyl-Alumoxanes.

FIG. 14 depicts a 3D representation of a carboxylate-alumoxane molecular structure.

FIG. 15 illustrates the structure and reactivity of Alkyl-Alumoxanes.

FIG. 17 depicts a synthesis scheme of Supra-Molecular Alkyl-Alumoxanes.

FIG. 18 depicts a synthesis scheme of the Polymerization Active Catalyst.

FIG. 21 is a Solid State NMR of Supported Solid Catalyst.

DETAILED DESCRIPTION OF THE PREFERRED EMBODIMENTS

The present invention discloses new heterogeneous solid supra-molecular alkylalumoxanes. In accordance with the invention, a supra-molecular architecture is created including a nano-particle foundation on which an alkylalumoxane is built. The supra-molecular alkylalumoxane comprises (a) an aluminum-oxide nanoparticle, (b) a linkage unit, and (c) an alkylalumoxane. The supra-molecular alkylalumoxanes are prepared by the reaction of a chemically modified aluminum-oxygen nanoparticle with either a pre-formed alkylalumoxane or an alkylaluminum compound with subsequent hydrolysis or reaction with other alkylalumoxane yielding reagents.

Figure 1:
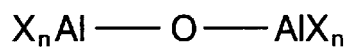
FIG. 1 is a representation of the simplest alumoxane.
Figure 2:
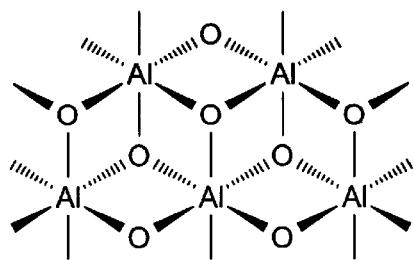
FIG. 2 is a schematic representation of the core structure of carboxylate-alumoxanes.
Figure 3:
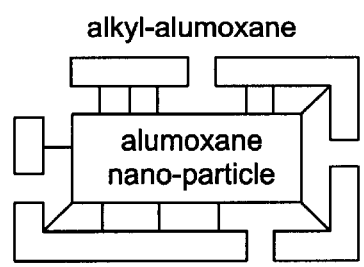
FIG. 3 is a schematic representation of solid supra-molecular alkylalumoxane.

Carboxylate-substituted alumoxanes have been well characterized (Landry et al. 1995 and Callender et al. 1997). Unlike the alkylalumoxanes, the carboxylate-alumoxanes have been shown to consist of an aluminum-oxygen nanoparticle core with a structure analogous to that found in the mineral boehmite, $[Al(O)(OH)]_n$ (FIG. 2), capped with carboxylate moieties. Solution particle size measurements show that carboxylate-alumoxanes are nano-particles with sizes ranging from 5–100 nm. The carboxylate ligand is bound to the aluminum surface and is only removed under extreme conditions. Carboxylate-alumoxanes previously reported have been limited to those prepared in water and with stability in air. Carboxylate-alumoxanes have to date, been limited to applications as ceramic precursors, have no catalytic activity, and are detrimental to co-catalysts. Surprisingly, the supramolecular alumoxanes of the present invention however, have high catalytic activity and are not detrimental to co-catalysts.

The carboxylate-substituted alumoxane nano-particles are prepared by the reaction of boehmite or pseudoboehmite with a carboxylic acid in a suitable solvent. The boehmite or pseudoboehmite source can be a commercial boehmite product such as Catapal (A, B, C, D, or FI, Vista Chemical Company) or boehmite prepared by the precipitation of aluminum nitrate with ammonium hydroxide, which is then hydrothermally treated or prepared by the hydrolysis of aluminum trialkoxides followed by hydrothermal treatment. The carboxylic acid can be any monocarboxylic acid with a substituent suitable to react with an aluminum alkyl or alkyl alumoxane. The carboxylic acid can be aromatic or aliphatic, and can contain hetero-atoms.

Suitable linkage units include hydroxyl, amine, and phosphine substituents. The linkage unit may either be incorporated during the synthesis of the nanoparticle or after synthesis of the nanoparticle. Examples of pre-formed linkage molecules include: para-hydroxybenzoic acid, gluconic acid, lysine, glycine, alanine, and threonine and related amine and hydroxide substituted acids among others. If the linkage unit is added after the creation of the nanoparticles, then examples of suitable reactions include: acylation or alkylation of benzoic acid. However, one of ordinary skill in the art will be able to design both pre-formed linkage units or the method for their synthesis by application of any number of well-known organic transformations (Larock, 1989). The design of the reactive termini which will become the joint to the alkylalumoxane may be any chemical group that is known to react with an aluminum alkyl or aluminum hydride (Wilkinson et al. 1983). It is not necessary that all the carboxylate substituents on the aluminum-oxide nanoparticle act as linkage units. If non-reactive carboxylate groups are present the surface concentration of active alkylalumoxane may be controlled.

Figure 4:
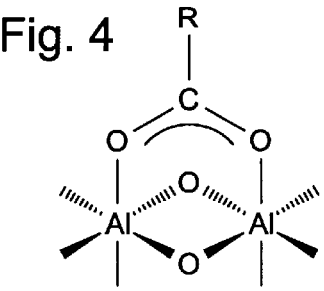
FIG. 4 is a schematic of the mode of coordination of the carboxylate linkage unit to the allunoxane nano-particle.
Figure 5:
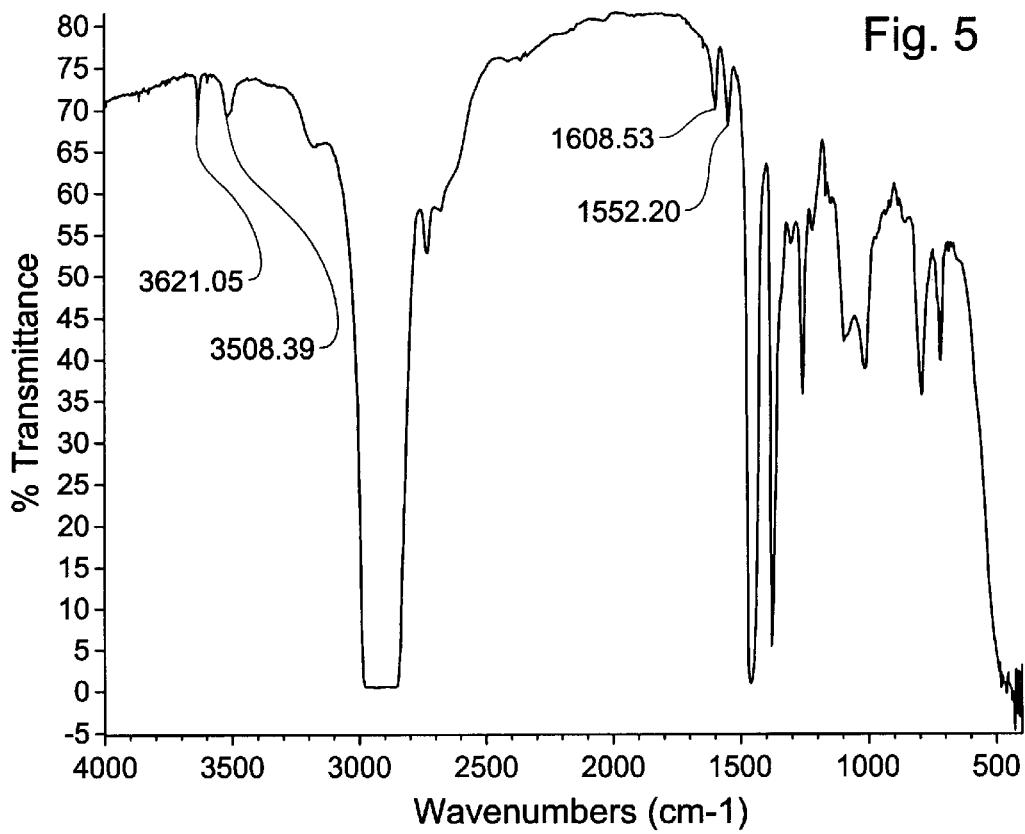
FIG. 5 is an Infrared Spectrum of methylalumoxane-hydroxybenzoate alumoxane resulting from the reaction of 4-hydroxybenoate alumoxane and methylalumoxane.
Figure 6:
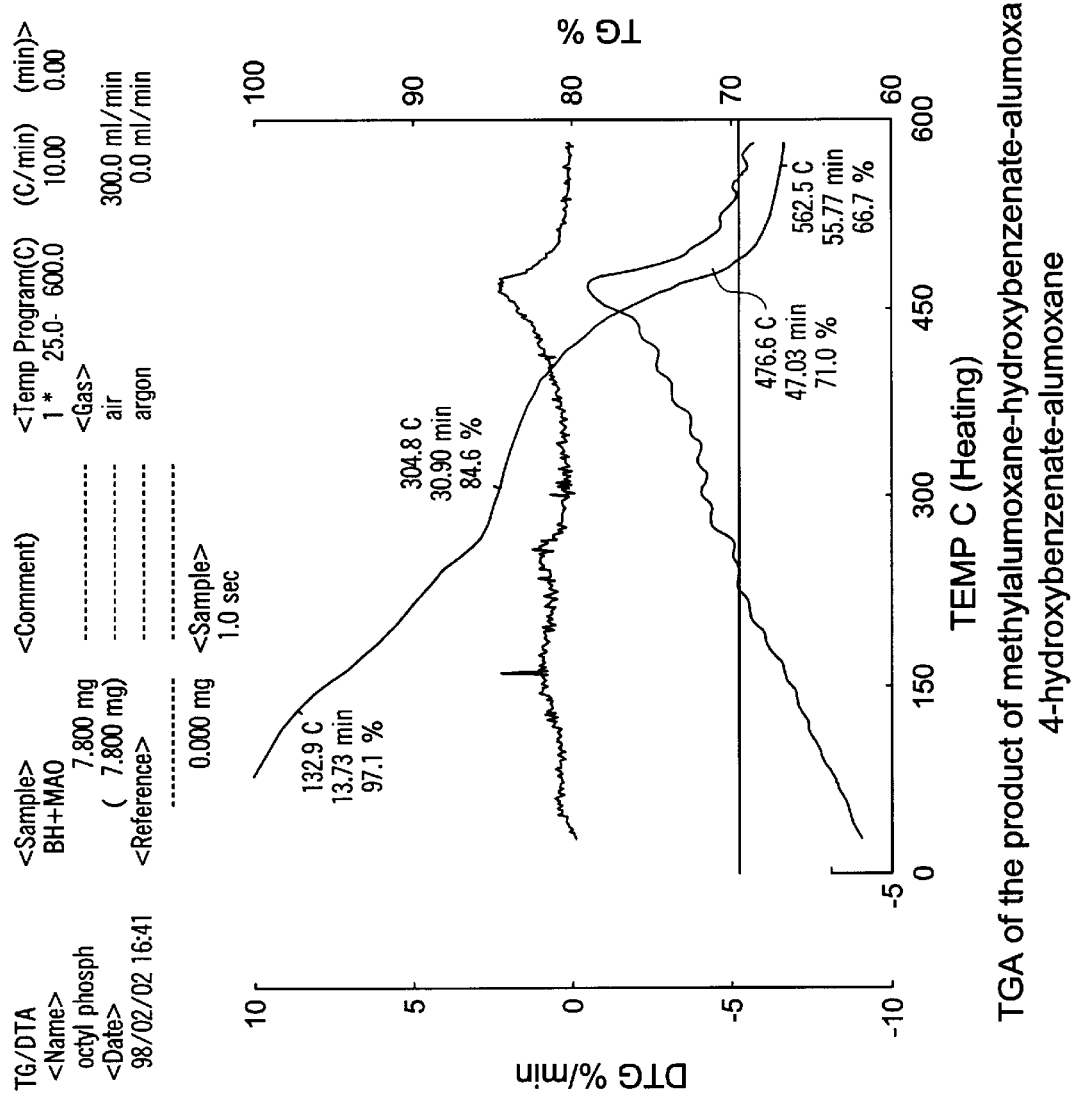
FIG. 6 is a TGA of methylalumoxane-hydroxybenzoate alumoxane resulting from the reaction of 4-hydroxybenoate alumoxane and methylalumoxane.
Figure 7:
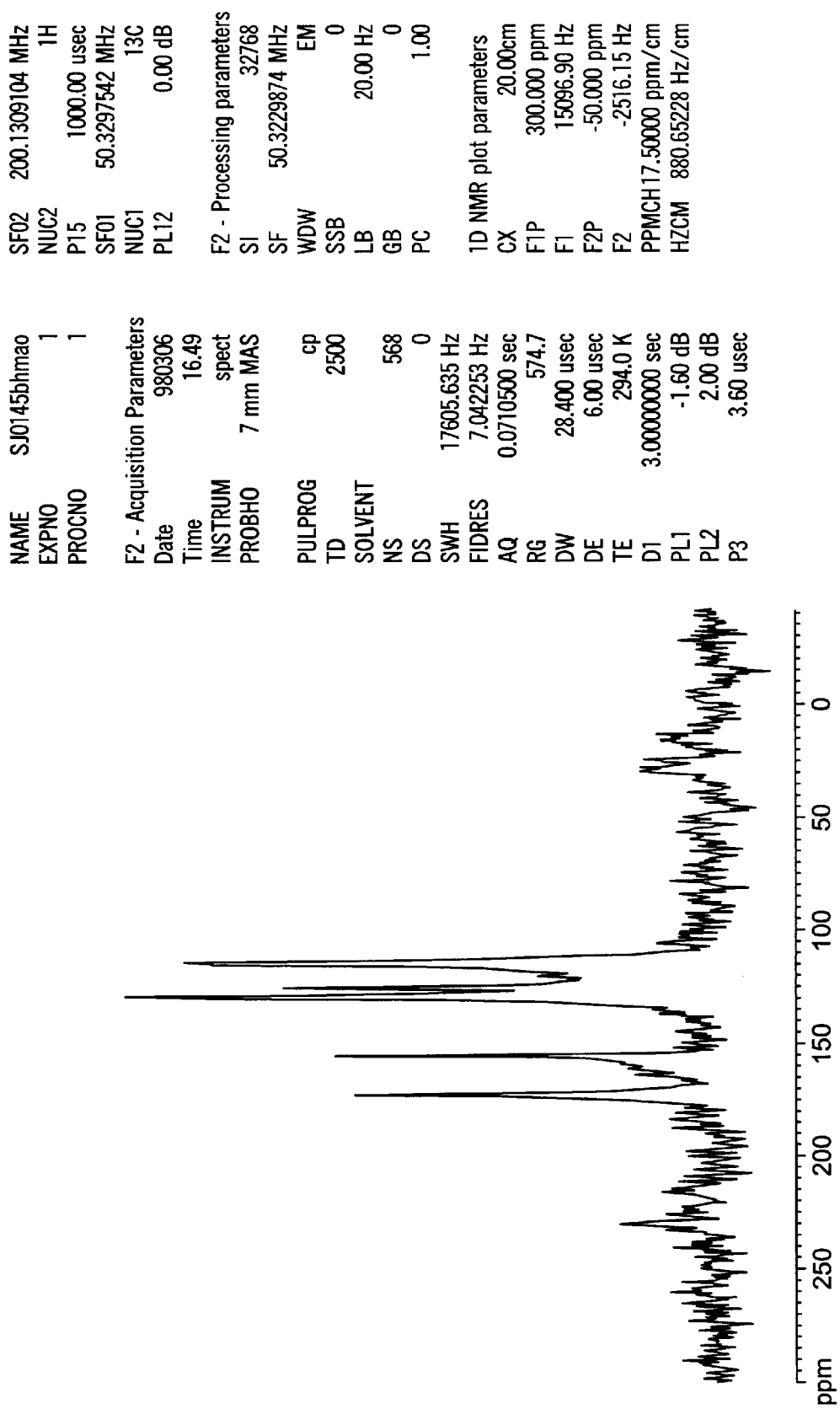
FIG. 7 is a Solid State NMR of methylalumoxane-hydroxybenxoate alumoxane resulting from the reaction of 4-hydroxybenoate alumoxane and methylalumoxane.
Figure 8:
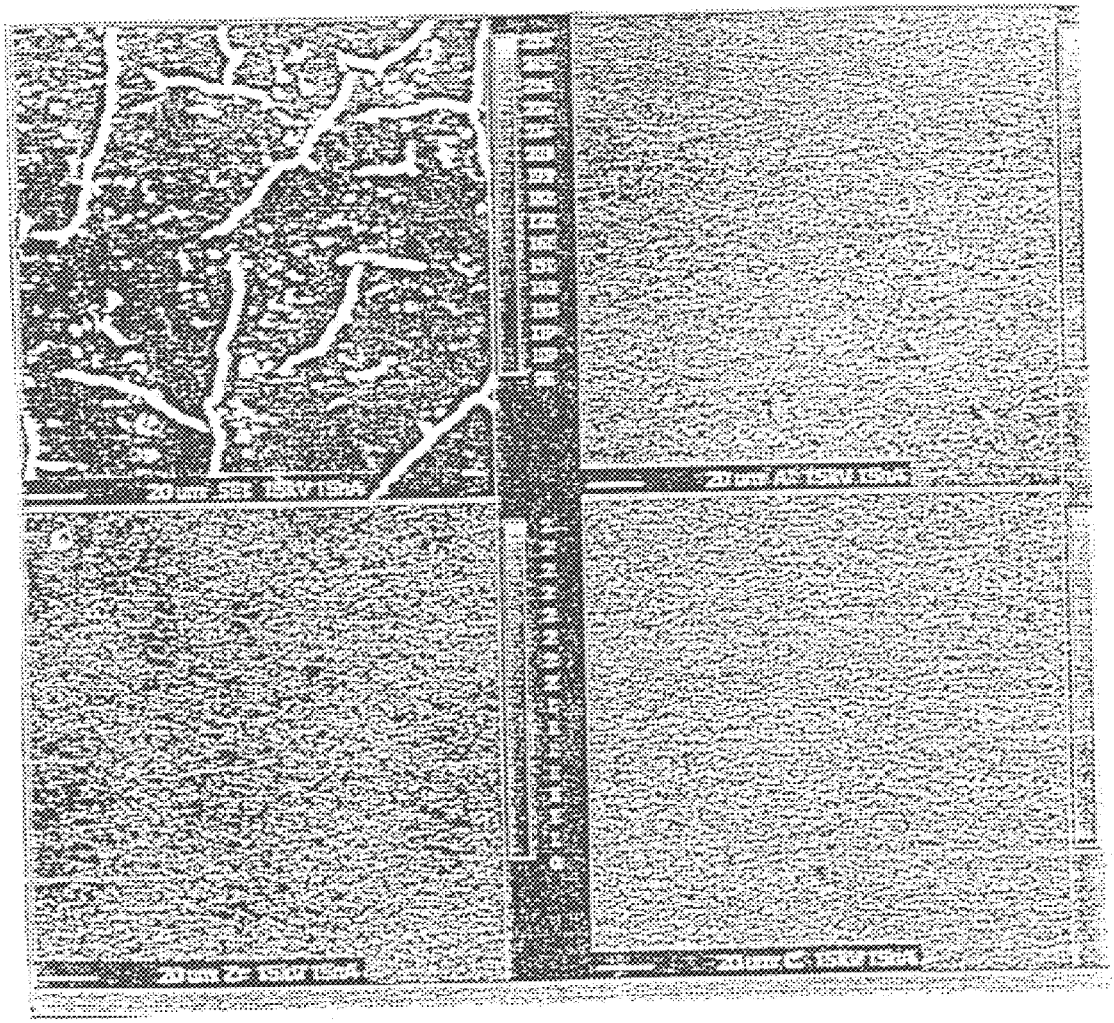
FIG. 8 is an electron dispersion spectroscopic analysis of methylalumoxane-hydroxybenzoate alumoxane after reaction with $Cp_2ZrCl_2$.
Figure 9:
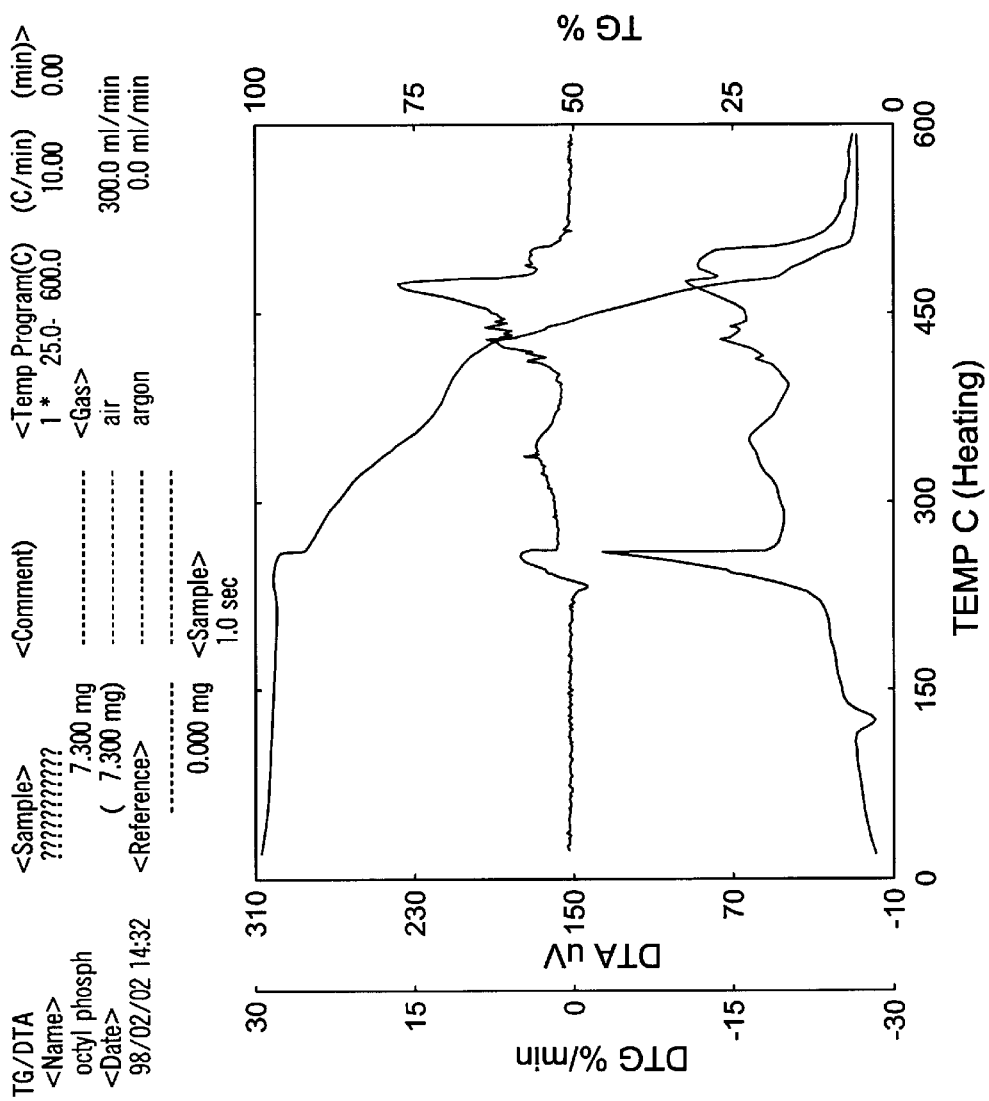
FIG. 9 is a thermogravimetric analysis of the polyethylene derived from the reaction of ethylene with methylalumoxane-hydroxybenzoate alumoxane/$Cp_2ZrCl_2$ catalyst.
Figure 10:
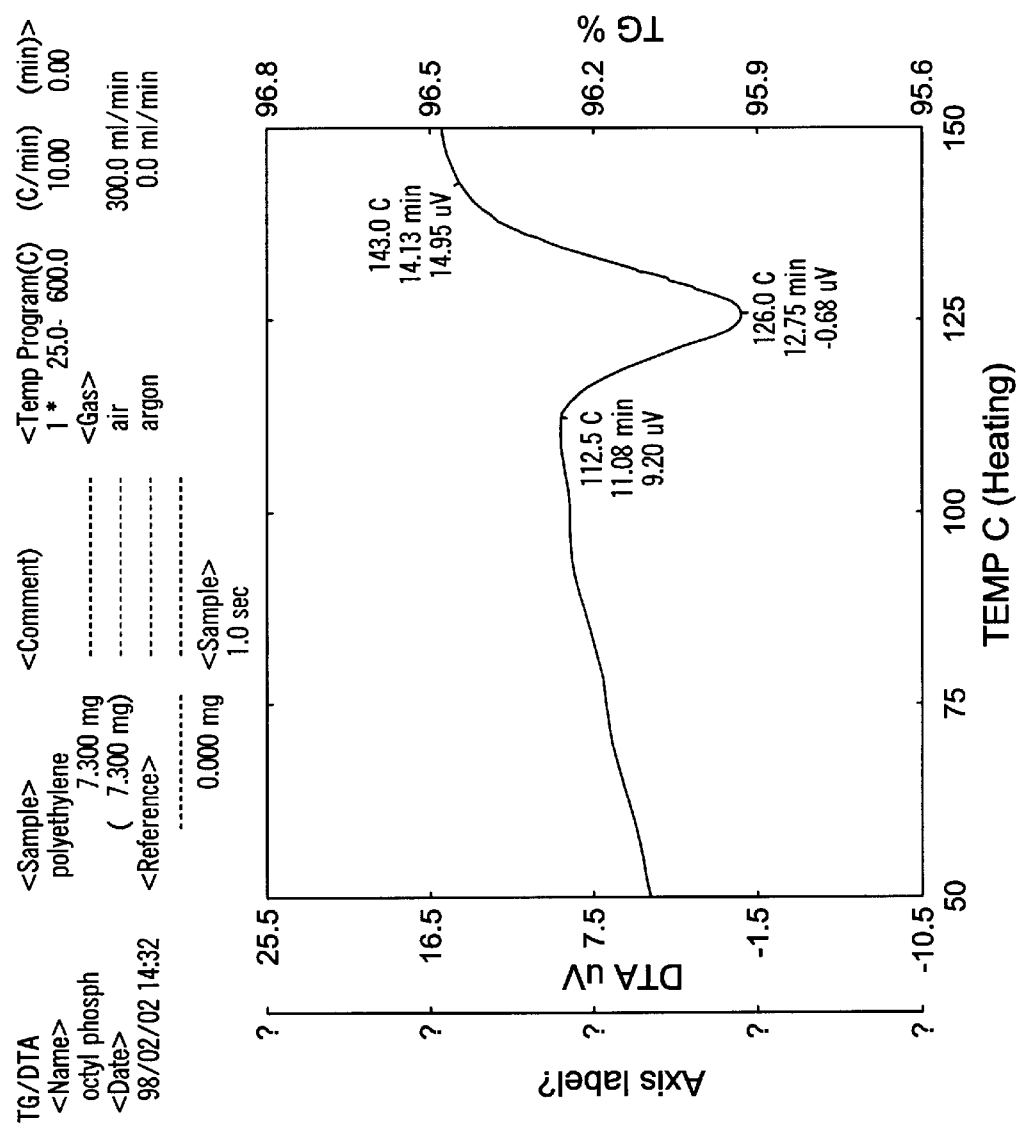
FIG. 10 is an expanded view of the DTA from thermogravimetric analysis of polyethylene derived from the reaction of ethylene with methylalumoxane-hydroxybenzoate alumoxane/$Cp_2ZrCl_2$ catalyst.
Figure 11:
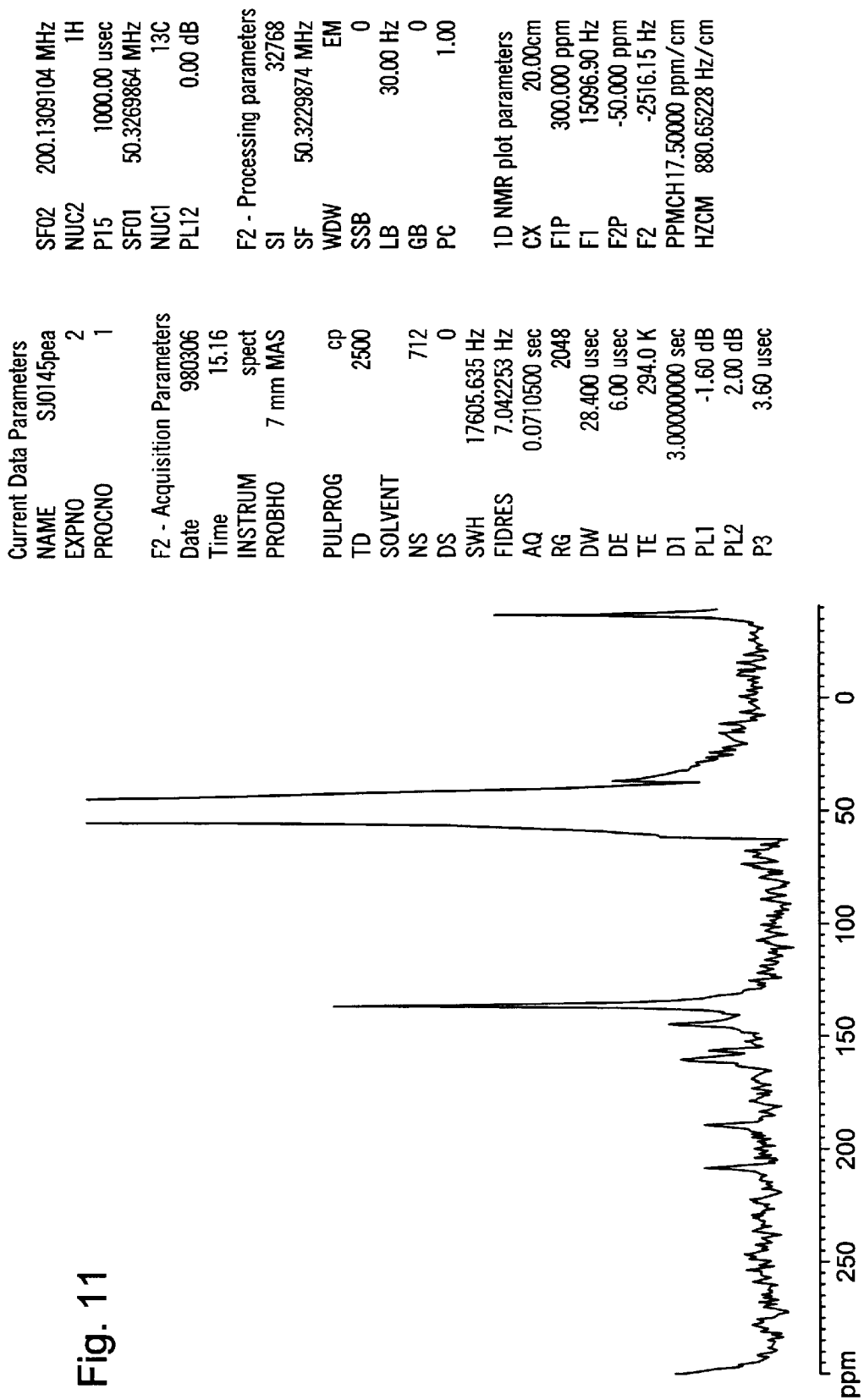
FIG. 11 is a Solid State NMR of polyethylene derived from the reaction of ethylene with methylalumoxane-hydroxybenzoate alumoxane/$Cp_2ZrCl_2$ catalyst.
Figure 12:
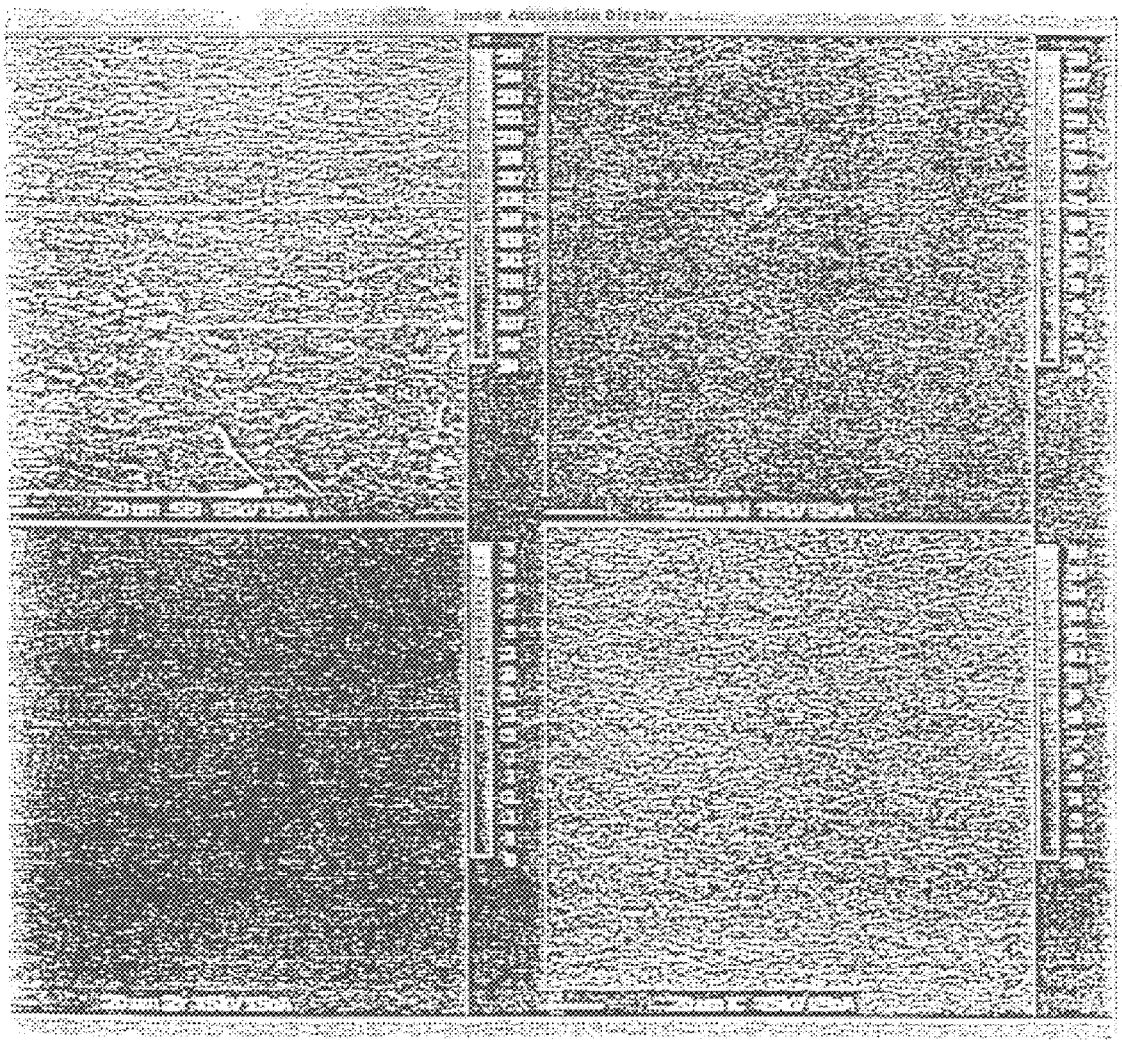
FIG. 12 is an electron dispersion spectroscopic analysis of polyethylene derived from the reaction of ethylene with methylalumoxane-hydroxybenzoate alumoxane/$Cp_2ZrCl_2$ catalyst.
Figure 16:
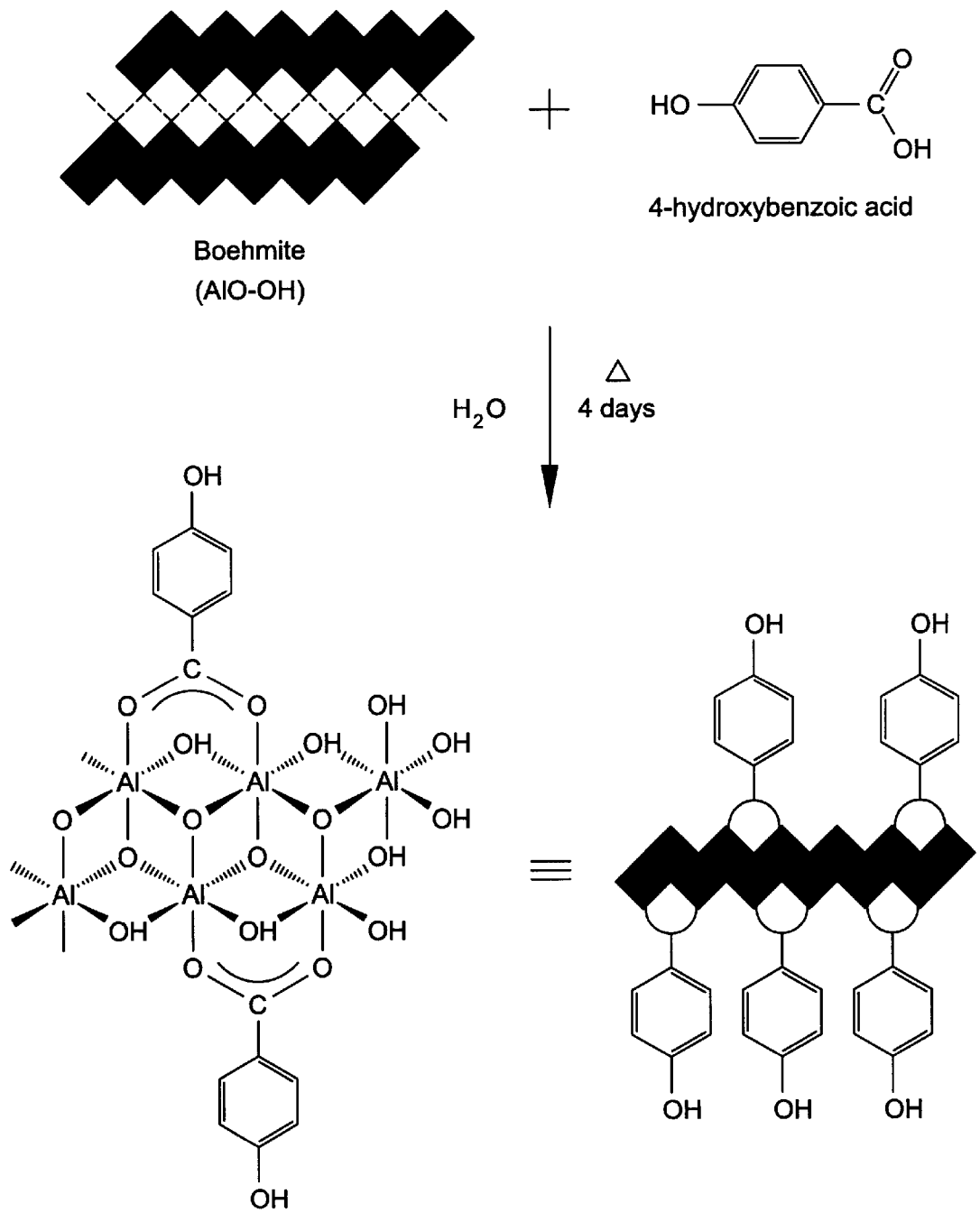
FIG. 16 depicts a synthesis scheme of 4-hydroxybenzoate alumoxane.
Figure 19A:
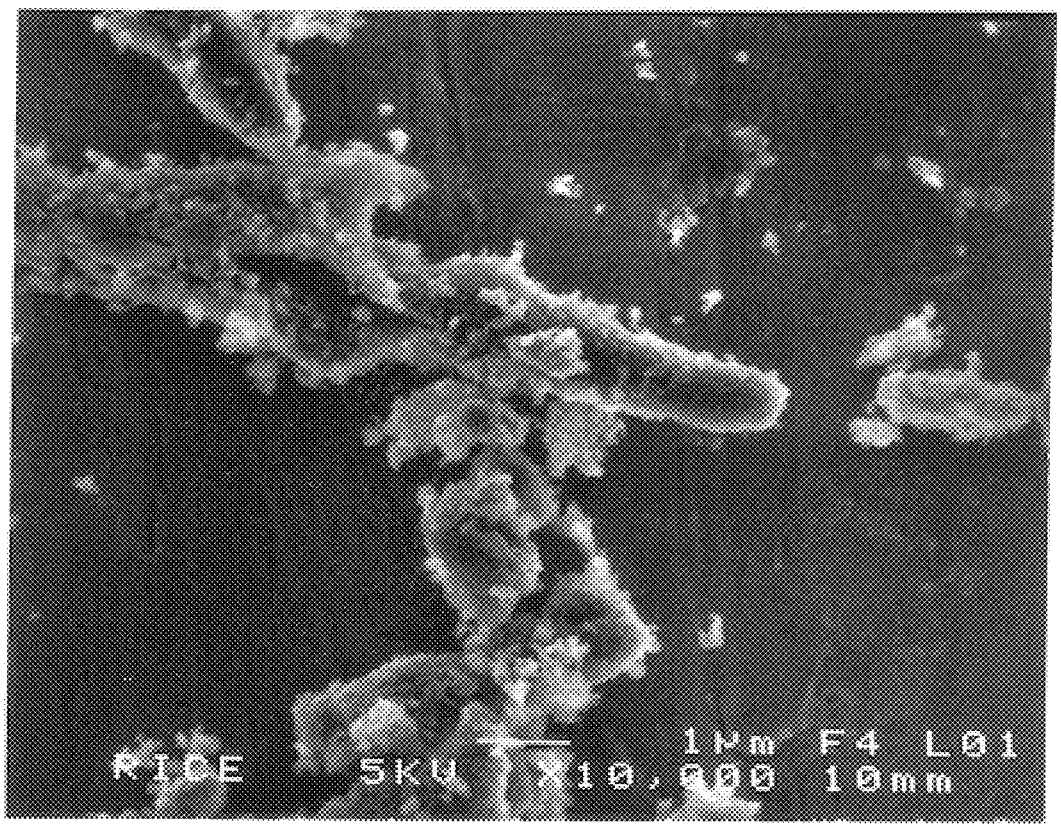
FIG. 19 shows SEM images of Supported Solid Catalyst.
Figure 19B:
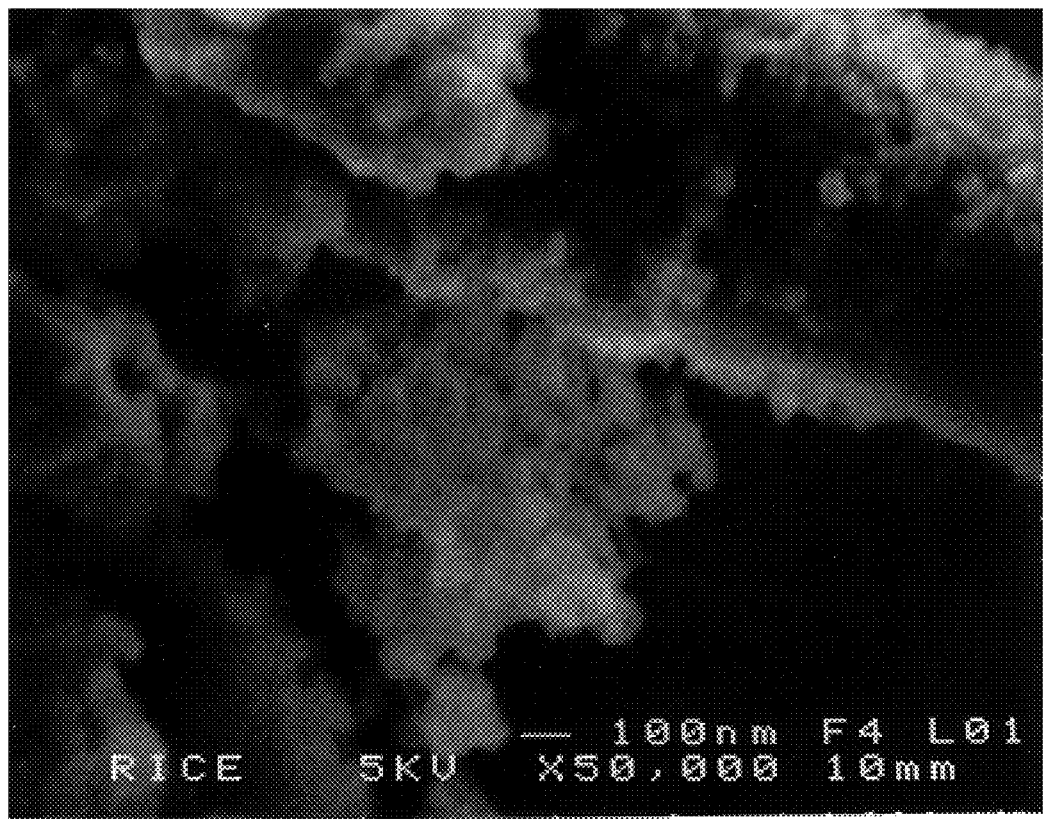
Figure 19C:
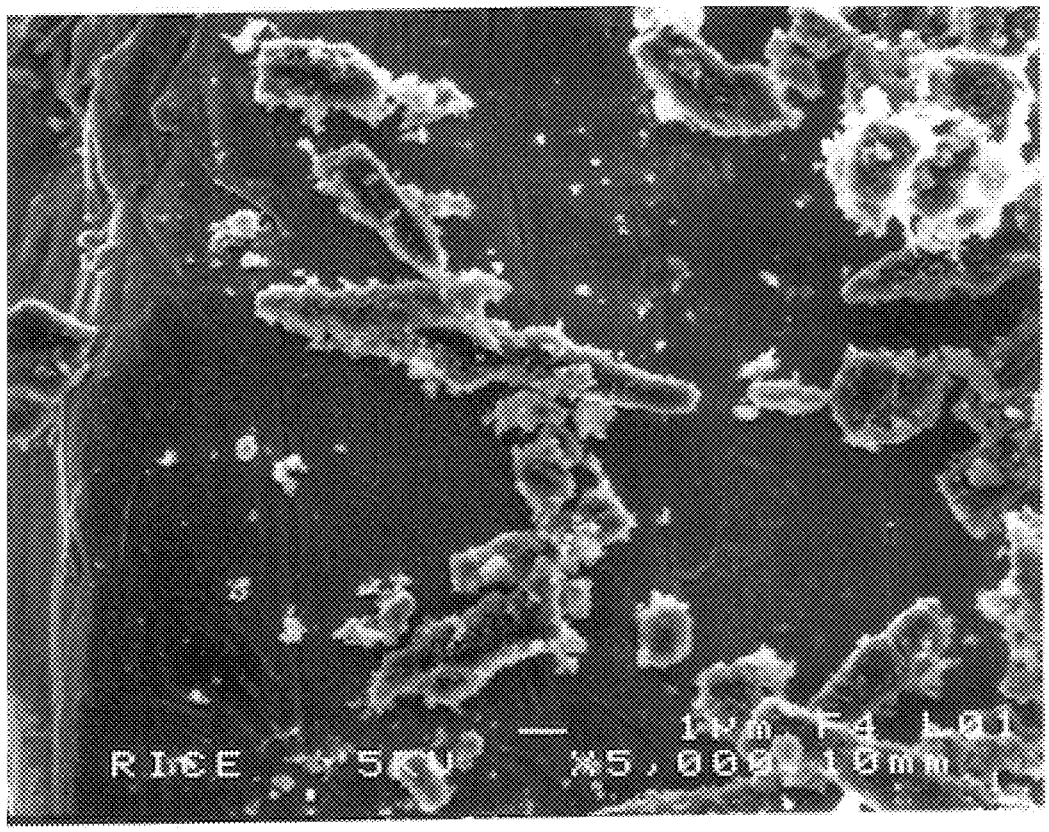
Figure 19D:
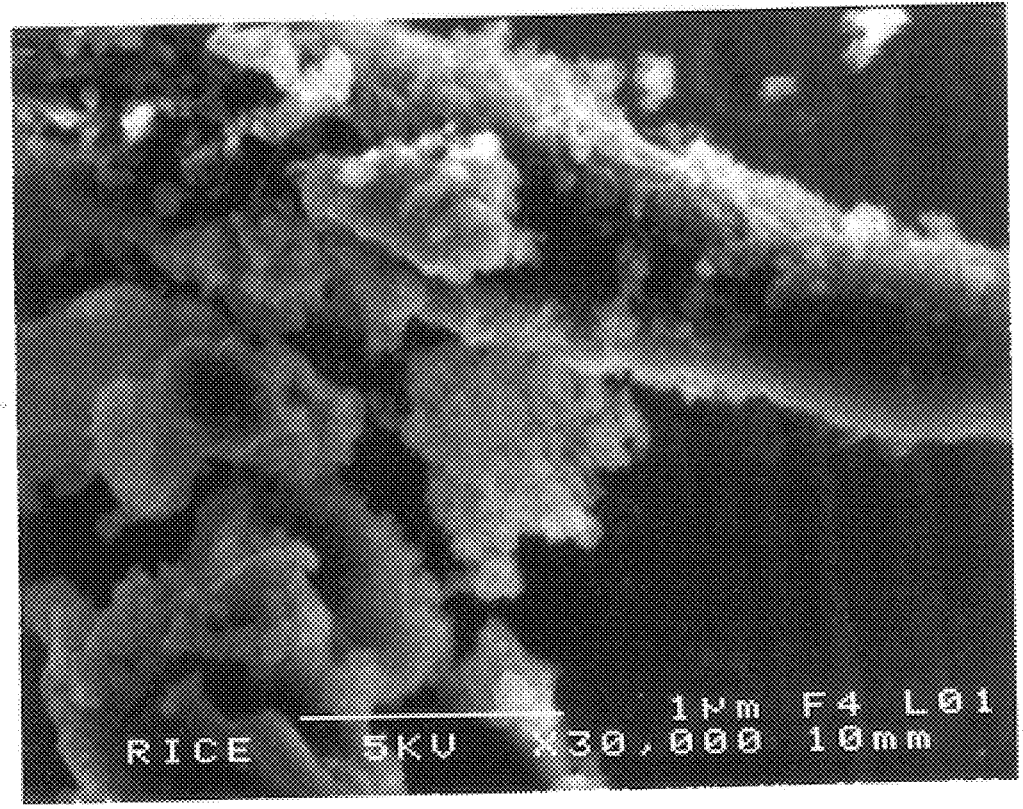
Figure 20:
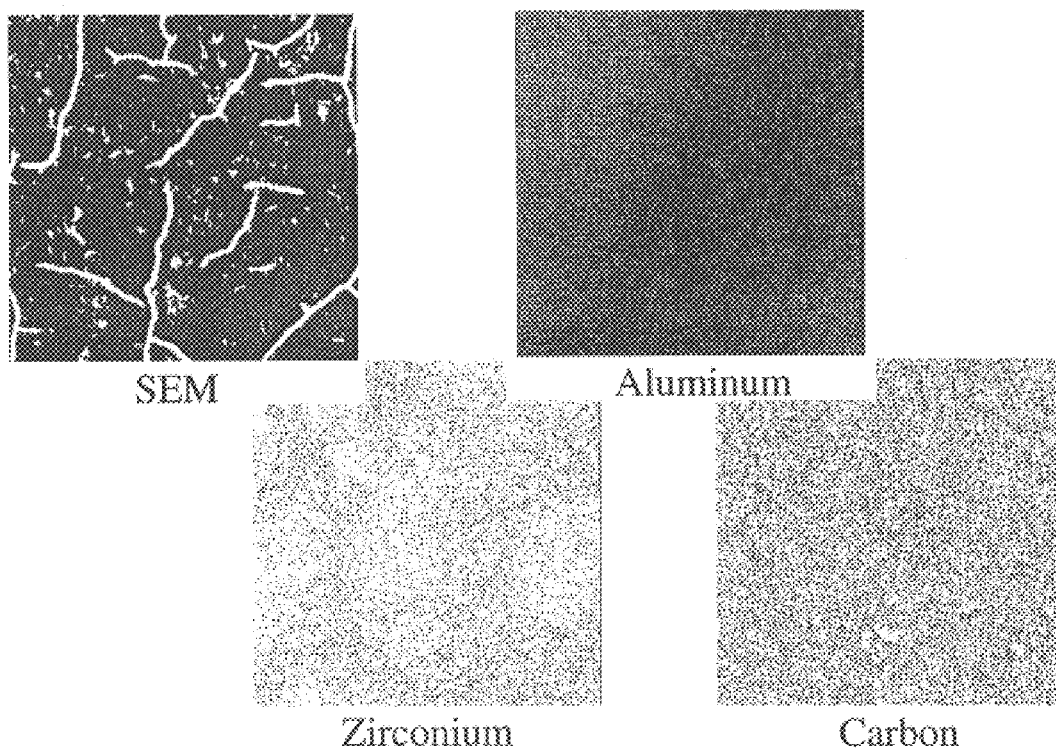
FIG. 20 shows microprobe images of Supported Solid Catalyst.
Figures 22, 25:
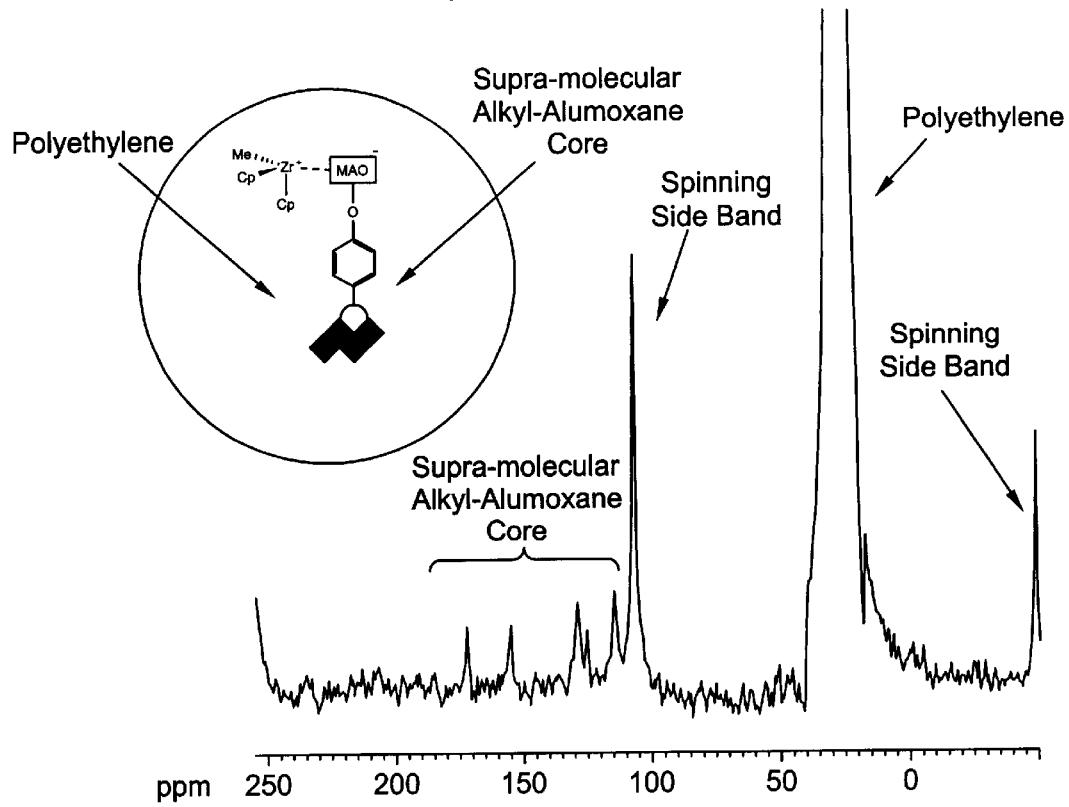
FIG. 22 shows data regarding the polymerization of Ethylene.
FIG. 25 is a Solid State NMR of Polyethylene from Supported Solid Catalyst.
Figure 23A:
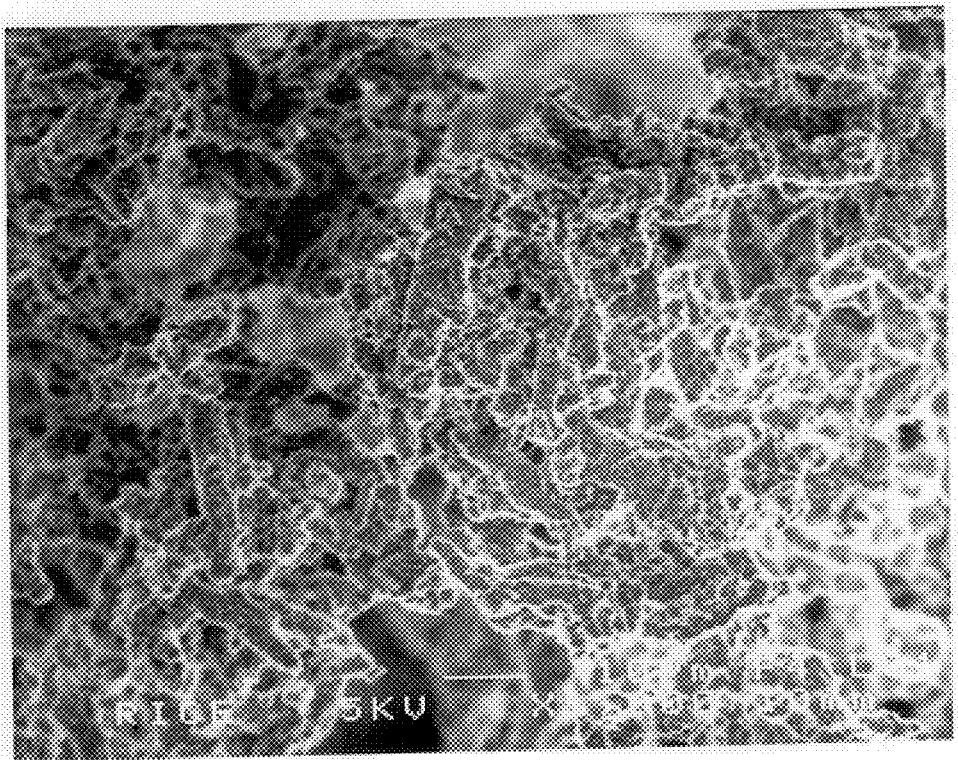
FIG. 23 shows SEM images of Polyethylene from Supported Solid Catalyst.
Figure 23B:
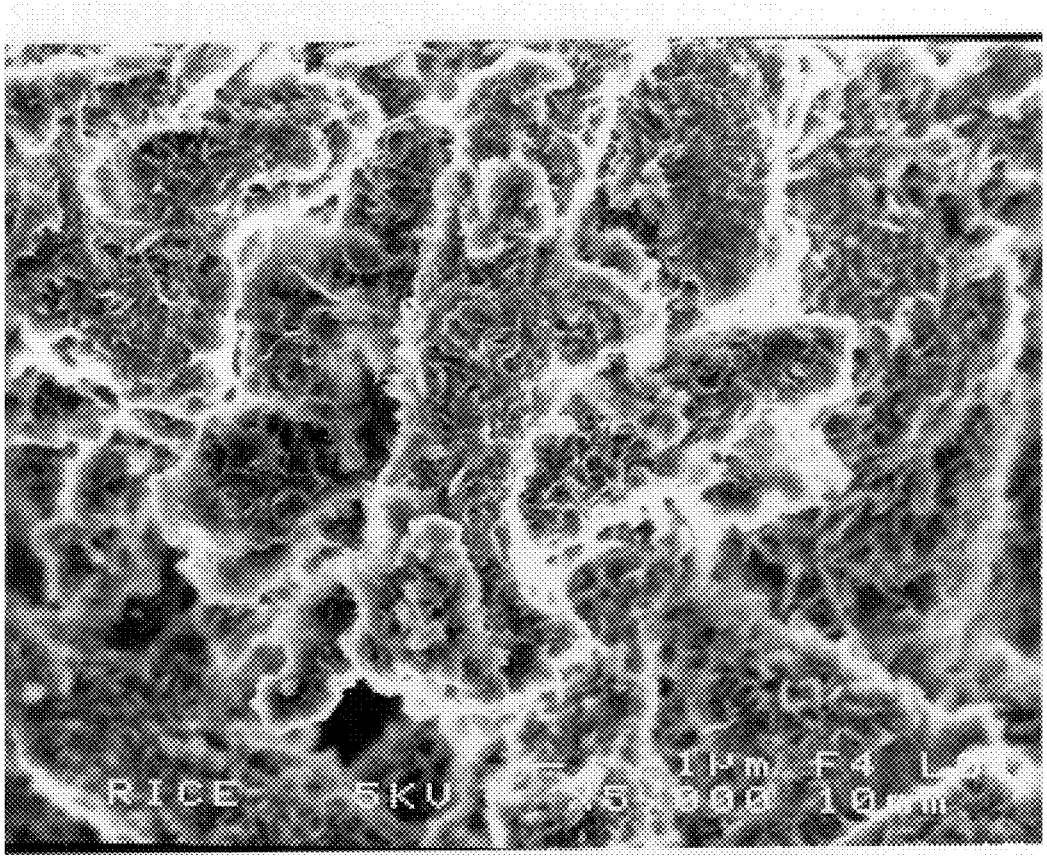
Figure 23C:
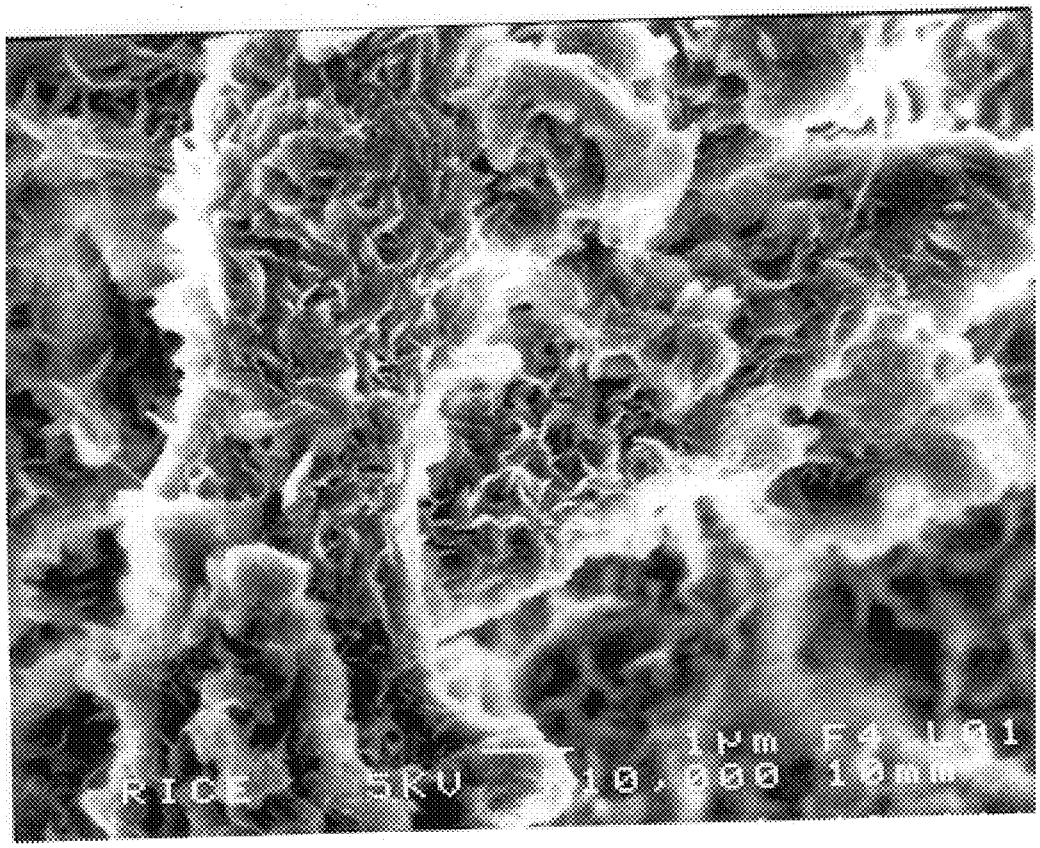
Figure 23D:
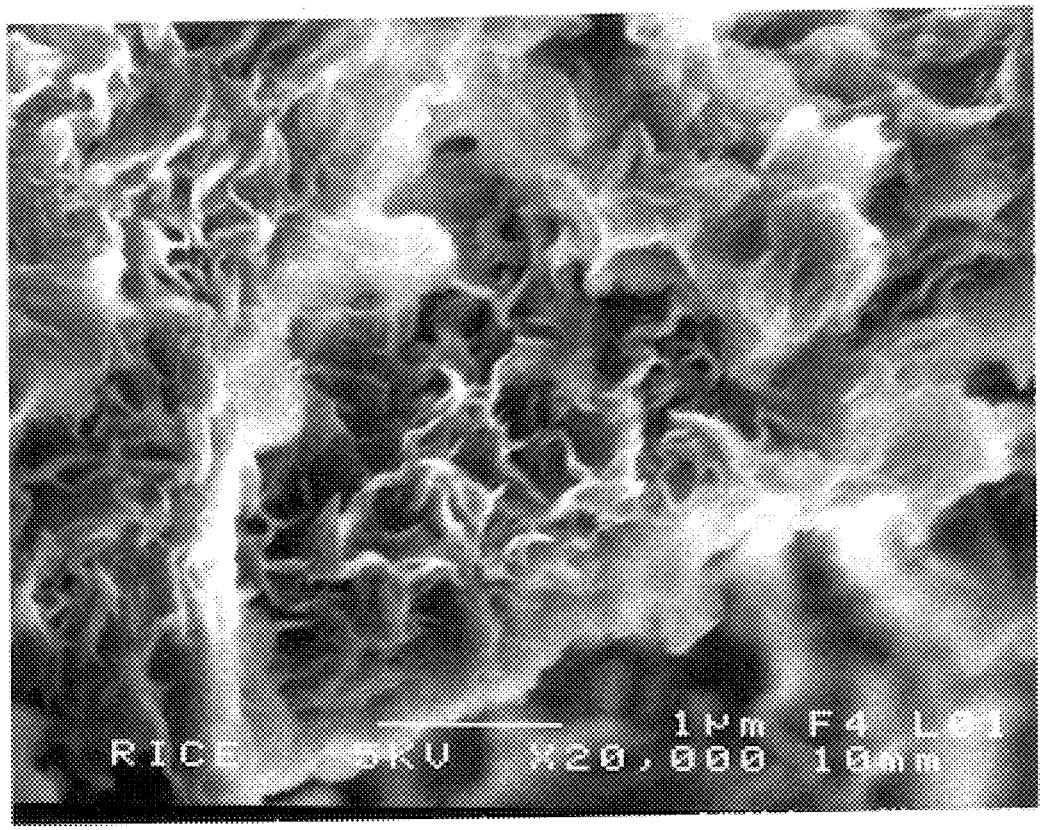
Figure 24:
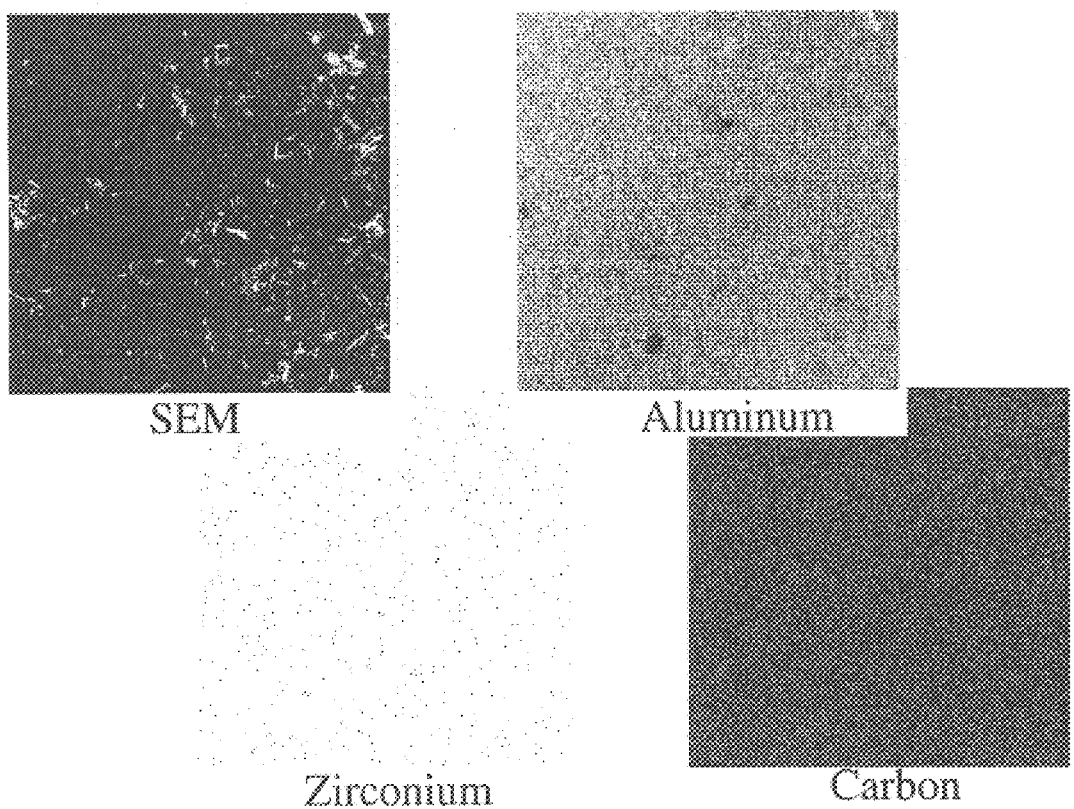
FIG. 24 shows microprobe images of Polyethylene from Supported Solid Catalyst.

A detailed description of one method of construction of a solid supra-molecular alkylalumoxane follows. The chemically modified carboxylato-alumoxane is prepared by mixing boehmite with para-hydroxybozoic acid as described below with Examples. The hydroxybenzoate-alumoxane is then reacted in toluene solution with methylalumoxane. The removal of the solvent under vacuum, followed by washing with toluene gives the supra-molecular alkylalumoxane. The physical appearance and solubility of the supra-molecular alkylalumoxane are similar to those of the parent alumoxanes. As with the parent alumoxanes, the doped-alumoxanes exist as 10–200 μm size particles, with a agglomerate size estimated from SEM to be less than 0.1 microns in diameter. The IR spectra of all the solid supra-molecular alkylalumoxane contain bands at 1608 and 1552 $cm^{-1}$, consistent with the retention of the bridging mode of coordination (FIG. 4) of the carboxylate to the boehmite core.

The use of solid supra-molecular alkylalumoxanes for catalysis offers significant advantages over supported alkylalumoxanes. The particle size is defined by the nanoparticle core and the concentration of active alkylalumoxane is controlled by the surface coverage of linkage units. Furthermore, the identity of the linkage unit may be used to alter the reactivity/activity of the alkylalumoxane catalyst component. While these advantages are significant, the alumoxanes have further benefits with respect to large scale production of alkylalumoxanes. The most dramatic is the simplicity of the methodology. The supra-molecular alkylalumoxane route of synthesis is simple and can be halted and/or modified at any stage without significant effect on the products. Another benefit with respect to large scale processing is the relatively low cost of the alumoxane precursors.

EXAMPLES

The following examples are presented to illustrate the ease and versatility of the approach and are not to be construed as limiting, in any way, the scope of the invention.

Example 1

Synthesis of 4-hydroxybenzenato-alumoxane.

4-hydroxybenzoic acid (50.0 g, 0.373 mol) was dissolved in water (800 mL) to which Vista Captal B boehmite (20 g, 0.338 mol) was slowly added, and the mixture was refluxed for 4 days. The resulting solution was cooled to room temperature and filtered. Washing with water, ethanol, ether, and toluene, yielded a white solid which was dried under vacuum. Yield 30.8 g. IR (1608 $cm^{-1}$, C—O, 1552 $cm^{-1}$, C—O). TGA of the hydroxybenzenato-alumoxane showed 24.8% ceramic yield (weight loss of 75.2%) which correlates with loss of 5.5 mmol of surface groups per gram of alumoxane.

Example 2

Synthesis of methylalumoxane-benzoatealumoxane

A solution of MAO in toluene (30%, 73.1 g) was added to a slurry of 4-hydroxybenzenato-alumoxane (10 g) in toluene (300 mL). The reaction mixture was stirred for 2 hours are room temperature then refluxed for 12 hours. The reaction was cooled to room temperature and filtered. The resulting white solid was washed with toluene (3×150 mL). The white solid was dried to yield 20.2 g. IR (1608 cm$^{-1}$, C—O, 1552 cm$^{-1}$, C—O)

Example 3

Polymerization of ethylene using methylalumoxane-hydroxybenzoatealumoxane

The metallocene catalyst was added to a slurry of methylalumoxane-benzenatoalumoxane (100 mg) in toluene (15 mL). Ethylene was bubbled through the solution at atmospheric pressure. The reaction mixture was quenched with methanol and filtered. The resulting white solid was dried and weighed.

Examples 4 to 21

Polymerization of ethylene using methylalumoxane-hydroxybenzoatealumoxane

The metallocene catalyst was added to a slurry of methylalumoxane-benzenatoalumoxane prepared as described in Tables 1, 2 and 3. Ethylene was bubbled through the solution at atmospheric pressure. The reaction mixture was quenched with methanol and filtered. The resulting white solid was dried and weighed.

TABLE 1

| Example | Cp$_2$ZrCl$_2$ (mg) | Alumoxane (mg) | Reaction Time (min.) | Yield (mg) | Activity (kg.mol cat$^{-1}$ · hr$^{-1}$) |
|---|---|---|---|---|---|
| 3 | 1 | 100 | 5 | 584 | 2748 |
| 4 | 1 | 100 | 10 | 944 | 2221 |
| 5 | 1 | 100 | 15 | 1270 | 1992 |
| 6 | 1 | 100 | 20 | 1033 | 1215 |
| 7 | 1 | 100 | 25 | 1945 | 1830 |
| 8 | 1 | 100 | 30 | 2041 | 1601 |
| 9 | 1 | 100 | 45 | 1317 | 688 |
| 10 | 1 | 100 | 60 | 1291 | 506 |

TABLE 2

| Example | Cp$_2$ZrCl$_2$ (mg) | Alumoxane (mg) | Reaction Time (min.) | Yield (mg) | Activity (kg.mol cat$^{-1}$ · hr$^{-1}$) |
|---|---|---|---|---|---|
| 11 | 0 | 100 | 5 | — | — |
| 12 | .005 | 100 | 5 | 92 | 86602 |
| 13 | .01 | 100 | 5 | 98 | 46125 |
| 14 | .05 | 100 | 5 | 181 | 17038 |
| 15 | .1 | 100 | 5 | 195 | 9177 |
| 16 | .5 | 100 | 5 | 491 | 4621 |
| 17 | 1 | 100 | 5 | 584 | 2748 |
| 18 | 2 | 100 | 5 | 521 | 1226 |
| 19 | 5 | 100 | 5 | 716 | 673 |
| 20 | 10 | 100 | 5 | 301 | 141 |

TABLE 3

| Example | (n-BuCp)$_2$ZrCl$_2$ (mg) | alumoxane (mg) | yield (mg) | Activity (kg.mol cat$^{-1}$ · hr$^{-1}$) |
|---|---|---|---|---|
| 21 | 1.0 | 100 | 2141 | 1730 |

REFERENCES

The following are incorporated herein in their entirety for all purposes:

Andreson, A., Cordes, H.-G., Herwig, J., Kaminsky, W., Merck, A., Mottweiler, R., Pein, J., Sinn, H., and Vollmer, H.-J., *Angew. Chem. Int. Ed. Engl.,* 15, 630 (1976).
Boleslawski, M., Pasynkiewicz, S., Jaworski, K., and Sadownik, A., *J. Organomet. Chem.,* 97, 15 (1975).
Callender, R. L. Harlan, C. J. Shapiro, N. M. Jones, C. D. Callahan, D. L. Weisner, M. R. Cook, R. Barron, A. R. *Chem. Mater.,* 1997, 9, 2418.
Colclough, R. O., *J. Polym. Sci.* 1959, 34, 178.
Gurian, P., Cheatham, L. K., Ziller J. W., and Barron, A. R., *J. Chem. Soc., Dalton Trans.,* 1449 (1991).
Harlan, C. J., Mason, M. R., and Barron, A. R., *Organometallics,* 13, 2957 (1994).
Harney, D. W., Meisters, A., and Mole, T., *Aust. J Chem.,* 27, 1639 (1974).
Kaminsky, W., Miri, M., Sinn, H., and Woldt, R., *Makromol. Chem., Rapid Commun.,* 4, 417 (1983).
Kushi, Y. and Frenando, Q., *J. Chem. Soc., Chem. Commun.,* 555 (1969).
Landry, C. C.; Davis, J. A.; Apblett, A. W.; Barron, A. R., *J. Mater. Chem.,* 3, 597 (1993).
Larock, R. C., *Comprehensive Organic Transformations,* VCH, New York (1989).
Long, W. P. and Breslow, D. S., *Leibigs Ann. Chem.,* 463 (1975).
Longiave. C; Castelli, R., *J. Polym. Sci.* 1963, 4C, 387.
Manyik, R. M., Walker, W. E., and Wilson, T. P., U.S. Pat. No. 3,242,099 (1966).
Mason, M. R. Smith, J. M. Bott, S. G., and Barron, A. R. *J. Am. Chem. Soc.,* 115, 4971 (1993).
Pajerski A. D. and Lenz, R. W. *Makromol. Chem. Macromol. Symp.,* 1993, 73, 7.
Razuvaev, G. A., Sangalov, Yu. A., Nel'kenbaum, Yu. Ya., and Minsker, K. S., *Izv. Akad. Nauk SSSR, Ser. Chim.,* 2547 (1975).
Reichert, K. H. and Meyer, K. R., *Macromol. Chem.,* 169, 163 (1973).
Saegusa, T., Fujii, Y., Fujii, H.; Furukawa, J., *Makromolek Chem.* 1962, 55, 232.
Sakharovskaya, G. B., Korneev, N. N., Popov, A. F., Kissin, Yu. V., Mezhkovskii, S. M., and Kristalanyi, E., *Zh. Obshch. Khim.,* 39, 788 (1969).
Sinn, H. and Kaminsky, W., *Adv. Organomet. Chem.,* 18, 99 (1980).
Ueyama, N., Araki, T., and Tani, H., *Inorg. Chem.,* 12, 2218 (1973).
Vandenberg, E. J., *J Polym. Sci.* 1960, 47, 489.
Vögtle, F., *Supramolecular Chemistry,* Wiley, N.Y. (1991).
Welborn, H. C., U.S. Pat. No. 4,808,561 (1989).
Wilkinson, G.; Stone, F. G. A.; Abel, E. W., Comprehensive Organometallic Chemistry, Pergamon Press (1983).
Winter, H., Schnuchel, W., and Sinn, H., *Macromol. Symp.* 97, 119 (1995).
Wynne, K. Y., *Inorg. Chem.,* 24, 1339 (1985).
Ziegler, K., *Angew. Chem.,* 68, 721 (1956).

We claim:

1. A supra-molecular alkylalumoxane, comprising a nanoparticle and an alumoxane.
2. The supra-molecular alkylalumoxanc of claim 1 wherein the alumoxane is an alkylalumoxane.
3. The supra-molecular alkylalumoxane of claim 2, further comprising a linkage unit.
4. The supra-molecular alkylalumoxane of claim 3 wherein the nanoparticle is an aluminum-oxide nanoparticle.
5. The supra-molecular alkylalumoxane of claim 4 wherein the alkylalumoxane is methylalumoxane.
6. The supra-molecular alkylalumoxane of claim 3 wherein the linkage unit comprises a carboxylate.

7. The supra-molecular alkylalumoxane of claim 3 wherein the linkage unit comprises at least one unit selected from the group consisting of OH, $NH_2$, NHR (where R is an organic group), carboxylate, SH, amide, $PH_2$, phosphate, phenyl, aromatic group, alkyl.

8. The supra-molecular alkylalumoxane of claim 7 wherein the nanoparticle is an aluminum-oxide nanoparticle.

9. The supra-molecular alkylalumoxane of claim 8 wherein the alkalyalumoxane is methylalumoxane.

10. The supra-molecular alkylalumoxane of claim 9 wherein the nanoparticle is between 5 and 100 nanometers in diameter.

11. The supra-molecular alkylalumoxane of claim 9 wherein the nanoparticle is between 10 and 70 nanometers in diameter.

12. The supra-molecular alkylalumoxane of claim 7 wherein the alkalyalumoxane is methylalumoxane.

13. The supra-molecular alkylalumoxane of claim 12 wherein the nanoparticle is between 5 and 100 nanometers in diameter.

14. The supra-molecular alkylalumoxane of claim 2 wherein the nanoparticle is an aluminum-oxide nanoparticle.

15. The supra-molecular alkylalumoxane of claim 1 wherein the nanoparticle is an aluminum-oxide nanoparticle.

16. A supra-molecular alkylalumoxane, comprising an alumoxane supported on a metal oxide nanoparticle.

17. The supra-molecular alkylalumoxane of claim 16 wherein the alumoxane is an alkylalumoxane.

18. The supra-molecular alkylalumoxane of claim 16 wherein the alkylalumoxane is methylalumoxane.

19. The supra-molecular alkylalumoxane of claim 16, further comprising a linkage unit.

20. The supra-molecular alkylalumoxane of claim 19 wherein the linkage unit is selected from the group consisting of hydroxyl, amine, and phosphine substituents and combinations thereof.

21. The supra-molecular alkylalumoxane of claim 19 wherein the linkage unit comprises a pre-formed linkage molecule selected from the group consisting of para-hydroxybenzoic acid, gluconic acid, lysine, glycine, alanine, and threonine and related amine and hydroxide substituted acids and combinations thereof.

22. The supra-molecular alkylalumoxane of claim 19 wherein the linkage unit comprises a carboxylate.

23. The supra-molecular alkylalumoxane of claim 16 wherein the nanoparticle comprises an aluminum-oxide nanoparticle.

24. The supra-molecular alkylalumoxane of claim 16 wherein the linkage unit comprises at least one unit selected from the group consisting of OH, $NH_2$, NHR (where R is an organic group), carboxylate, SH, amide, $PH_2$, phosphate, phenyl, aromatic group, alkyl.

25. The supra-molecular alkylalumoxane of claim 16 wherein the nanoparticle is between 5 and 100 nanometers in diameter.

* * * * *